US010835199B2

(12) United States Patent
Chtcheprov et al.

(10) Patent No.: US 10,835,199 B2
(45) Date of Patent: Nov. 17, 2020

(54) OPTICAL GEOMETRY CALIBRATION DEVICES, SYSTEMS, AND RELATED METHODS FOR THREE DIMENSIONAL X-RAY IMAGING

(71) Applicant: The University of North Carolina at Chapel Hill, Chapel Hill, NC (US)

(72) Inventors: Pavel Chtcheprov, Chapel Hill, NC (US); Otto Z. Zhou, Chapel Hill, NC (US); Jianping Lu, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 489 days.

(21) Appl. No.: 15/421,869

(22) Filed: Feb. 1, 2017

(65) Prior Publication Data

US 2017/0219498 A1 Aug. 3, 2017

Related U.S. Application Data

(60) Provisional application No. 62/289,714, filed on Feb. 1, 2016.

(51) Int. Cl.
*A61B 6/00* (2006.01)
*G01N 23/046* (2018.01)
(Continued)

(52) U.S. Cl.
CPC ............ *A61B 6/584* (2013.01); *A61B 5/0037* (2013.01); *A61B 6/04* (2013.01); *A61B 6/0492* (2013.01);
(Continued)

(58) Field of Classification Search
CPC ............ G01N 23/046; G01N 2223/30; G01N 2223/302; G01N 2223/303;
(Continued)

(56) References Cited

U.S. PATENT DOCUMENTS 3,617,285 A 11/1971 Staudenmayer
3,733,484 A 5/1973 Bayard
(Continued)

FOREIGN PATENT DOCUMENTS

CN 2336381 Y 9/1999
CN 2440535 8/2001
(Continued)

OTHER PUBLICATIONS

Dobbins III, J.T., et al., "Digital x-ray tomosynthesis: current state of the art and clinical potential," Phys. Med. Biol. 48, pp. R65-R106 (2003).
(Continued)

*Primary Examiner* — Anastasia Midkiff
(74) *Attorney, Agent, or Firm* — Jenkins, Wilson, Taylor & Hunt, P.A.

(57) ABSTRACT

Optical geometry calibration devices, systems, and related methods for x-ray imaging are disclosed. An optical-based geometry calibration device is configured to interface with a two-dimensional (2D) imaging device to perform three-dimensional (3D) imaging. The optical-based geometry calibration device includes one or more optical cameras fixed to either an x-ray source or an x-ray detector, one or more markers fixed to the x-ray detector or the x-ray source, with each of the one or more optical cameras being configured to capture at least one photographic image of one or more corresponding optical markers when each x-ray image of the object is captured, and an image processing system configured to compute positions of the x-ray source relative to the x-ray detector for each 2D projection image based on the at least one photographic image of the one or more markers.

18 Claims, 14 Drawing Sheets

(51) Int. Cl.
*A61B 6/04* (2006.01)
*A61B 5/00* (2006.01)
*G01T 1/29* (2006.01)
*G01T 7/00* (2006.01)
*A61B 34/20* (2016.01)
*A61B 90/00* (2016.01)

(52) U.S. Cl.
CPC .............. *A61B 6/582* (2013.01); *A61B 6/583* (2013.01); *A61B 6/585* (2013.01); *G01N 23/046* (2013.01); *G01T 1/2978* (2013.01); *G01T 7/005* (2013.01); *A61B 2034/2065* (2016.02); *A61B 2090/367* (2016.02); *A61B 2560/0228* (2013.01); *G01N 2223/302* (2013.01); *G01N 2223/303* (2013.01)

(58) Field of Classification Search
CPC ... G01N 2223/3035; G01N 2223/3037; G01N 2223/323; G01N 2223/34; G01N 2223/419; A61B 5/00; A61B 5/0033; A61B 5/0035; A61B 5/0037; A61B 5/70; A61B 5/706; A61B 6/00; A61B 6/02; A61B 6/03; A61B 6/032; A61B 6/035; A61B 6/04; A61B 6/0492; A61B 6/08; A61B 6/14; A61B 6/145; A61B 6/58; A61B 6/582–585; A61B 6/587; A61B 2034/2055; A61B 2034/2057; A61B 2034/2065; A61B 90/30; A61B 90/36; A61B 90/361; A61B 2090/0807; A61B 2090/0811; A61B 2090/364; A61B 2090/365; A61B 2090/367; A61B 2560/00; A61B 2560/02; A61B 2560/0223; A61B 2560/0228; A61B 2560/0233; A61B 2560/0238; A61B 2560/04; A61B 2560/0406; A61B 2560/0443; A61B 2560/06; G01T 1/2978; G01T 7/00; G01T 7/005; H01J 35/14; H01J 35/153; H01J 37/00; H01J 37/02; H01J 37/22; H01J 37/244; H01J 2237/00; H01J 2237/15; H01J 2237/1501; H01J 2237/1502; H01J 2237/1504; H01J 2237/245; H01J 2237/24507; H01J 2237/24514; H01J 2237/24528; H01J 2237/24542; H01J 2237/24578; H01J 2237/24592; H01J 2237/248; H01J 2237/2482
See application file for complete search history.

(56) References Cited

U.S. PATENT DOCUMENTS

| | | |
|---|---|---|
| 3,783,288 A | 1/1974 | Barbour et al. |
| 3,921,022 A | 11/1975 | Levine |
| 3,932,756 A | 1/1976 | Cowell et al. |
| 4,253,221 A | 3/1981 | Cochran, Jr. et al. |
| 4,712,226 A | 12/1987 | Horbaschek |
| 4,728,576 A | 3/1988 | Gillberg-LaForce et al. |
| 4,809,308 A | 2/1989 | Adams et al. |
| 4,926,452 A | 5/1990 | Baker et al. |
| 5,129,850 A | 7/1992 | Kane et al. |
| 5,138,237 A | 8/1992 | Kane et al. |
| 5,241,578 A | 8/1993 | MacMahon |
| 5,245,648 A | 9/1993 | Kinney et al. |
| 5,317,618 A | 5/1994 | Nakahara et al. |
| 5,412,703 A | 5/1995 | Goodenough et al. |
| 5,424,054 A | 6/1995 | Bethune et al. |
| 5,594,770 A | 1/1997 | Bowles et al. |
| 5,616,368 A | 4/1997 | Jin et al. |
| 5,623,180 A | 4/1997 | Jin et al. |
| 5,637,950 A | 6/1997 | Jin et al. |
| 5,648,699 A | 7/1997 | Jin et al. |
| 5,692,028 A | 11/1997 | Geus et al. |
| 5,726,524 A | 3/1998 | Debe |
| 5,745,437 A | 4/1998 | Wachter et al. |
| 5,764,683 A | 6/1998 | Swift et al. |
| 5,773,834 A | 6/1998 | Yamamoto et al. |
| 5,786,895 A | 7/1998 | Mitchell et al. |
| 5,828,722 A | 10/1998 | Ploetz et al. |
| 5,973,444 A | 10/1999 | Xu et al. |
| RE36,415 E | 11/1999 | McKenna |
| 6,019,656 A | 2/2000 | Park et al. |
| 6,028,911 A | 2/2000 | Kawahara |
| 6,057,637 A | 5/2000 | Zettl et al. |
| 6,087,765 A | 7/2000 | Coll et al. |
| 6,097,138 A | 8/2000 | Nakamoto |
| 6,097,788 A | 8/2000 | Berenstein et al. |
| 6,125,167 A | 9/2000 | Morgan |
| 6,165,181 A * | 12/2000 | Heilbrun .................. A61B 5/06 606/130 |
| 6,178,226 B1 | 1/2001 | Hell et al. |
| 6,192,104 B1 | 2/2001 | Adams et al. |
| 6,250,984 B1 | 6/2001 | Jin et al. |
| 6,277,138 B1 | 8/2001 | Levinson et al. |
| 6,277,318 B1 | 8/2001 | Bower et al. |
| 6,280,697 B1 | 8/2001 | Zhou et al. |
| 6,334,939 B1 | 1/2002 | Zhou et al. |
| 6,440,761 B1 | 8/2002 | Choi |
| 6,445,122 B1 | 9/2002 | Chuang et al. |
| 6,447,163 B1 * | 9/2002 | Bani-Hashemi ......... A61B 6/08 378/205 |
| 6,459,767 B1 | 10/2002 | Boyer et al. |
| 6,498,349 B1 | 12/2002 | Thomas et al. |
| 6,510,195 B1 | 1/2003 | Chappo et al. |
| 6,545,396 B1 | 4/2003 | Ohki et al. |
| 6,621,887 B2 | 9/2003 | Albagli et al. |
| 6,630,772 B1 | 10/2003 | Bower et al. |
| 6,650,730 B2 | 11/2003 | Bogatu et al. |
| 6,674,837 B1 | 1/2004 | Taskar et al. |
| 6,753,931 B2 | 6/2004 | Kane et al. |
| 6,760,407 B2 | 7/2004 | Price et al. |
| RE38,561 E | 8/2004 | Keesmann et al. |
| 6,787,122 B2 | 9/2004 | Zhou |
| 6,850,595 B2 | 2/2005 | Zhou et al. |
| 6,852,973 B2 | 2/2005 | Suzuki et al. |
| 6,876,724 B2 | 4/2005 | Zhou et al. |
| 6,885,022 B2 | 4/2005 | Yaniv et al. |
| 6,914,959 B2 | 7/2005 | Bailey et al. |
| 6,917,664 B2 | 7/2005 | Chappo et al. |
| 6,940,943 B2 | 9/2005 | Hermann et al. |
| 6,949,877 B2 | 9/2005 | Sun et al. |
| 6,965,199 B2 | 11/2005 | Stoner et al. |
| 6,980,627 B2 | 12/2005 | Qiu et al. |
| 6,999,554 B2 | 2/2006 | Mertelmeier |
| 7,027,558 B2 | 4/2006 | Ghelmansarai et al. |
| 7,046,757 B1 | 5/2006 | Bani-Hashemi et al. |
| 7,082,182 B2 | 7/2006 | Zhou et al. |
| 7,085,351 B2 | 8/2006 | Lu et al. |
| 7,103,137 B2 | 9/2006 | Seppi et al. |
| 7,129,513 B2 | 10/2006 | Zhou et al. |
| 7,147,894 B2 | 12/2006 | Zhou et al. |
| 7,187,756 B2 | 3/2007 | Gohno et al. |
| 7,192,031 B2 | 3/2007 | Dunham et al. |
| 7,227,924 B2 | 6/2007 | Zhou et al. |
| 7,245,692 B2 | 7/2007 | Lu et al. |
| 7,245,694 B2 | 7/2007 | Jing et al. |
| 7,252,749 B2 | 8/2007 | Zhou et al. |
| 7,294,248 B2 | 11/2007 | Gao |
| 7,330,529 B2 | 2/2008 | Kautzer et al. |
| 7,359,484 B2 | 4/2008 | Qiu et al. |
| 7,428,298 B2 | 9/2008 | Bard et al. |
| 7,440,603 B2 | 10/2008 | Eberhard et al. |
| 7,581,884 B1 * | 9/2009 | Barnes ..................... A61B 6/06 378/164 |
| 7,639,775 B2 | 12/2009 | DeMan et al. |
| 7,656,999 B2 | 2/2010 | Hui et al. |
| 7,736,055 B2 * | 6/2010 | Hornig ..................... A61B 6/08 378/206 |
| 7,741,624 B1 | 6/2010 | Sahadevan |

(56) References Cited

U.S. PATENT DOCUMENTS

| | | | |
|---|---|---|---|
| 7,751,528 B2 | 7/2010 | Zhou et al. | |
| 7,835,492 B1 | 11/2010 | Sahadevan | |
| 7,887,689 B2 | 2/2011 | Zhou et al. | |
| 7,902,530 B1 | 3/2011 | Sahadevan | |
| 7,940,887 B2 | 5/2011 | Shibata et al. | |
| 8,576,988 B2 | 11/2013 | Lewalter et al. | |
| 8,670,521 B2 | 3/2014 | Bothorel et al. | |
| 8,821,015 B2* | 9/2014 | Stagnitto | A61B 6/4291 378/205 |
| 8,873,712 B2* | 10/2014 | Wang | A61B 6/08 378/97 |
| 9,036,775 B2 | 5/2015 | Yoshikawa et al. | |
| 9,299,190 B2 | 3/2016 | Koivisto et al. | |
| 9,438,897 B2* | 9/2016 | Barreto | H04N 17/002 |
| 9,782,136 B2* | 10/2017 | Zhou | A61B 6/547 |
| 9,907,520 B2* | 3/2018 | Zhou | A61B 6/547 |
| 10,539,708 B2 | 1/2020 | Zhou et al. | |
| 2002/0041655 A1* | 4/2002 | Mitschke | A61B 6/547 378/207 |
| 2002/0080921 A1 | 6/2002 | Smith et al. | |
| 2002/0085674 A1 | 7/2002 | Price et al. | |
| 2002/0110996 A1 | 8/2002 | Yaniv et al. | |
| 2002/0140336 A1 | 10/2002 | Stoner et al. | |
| 2002/0171357 A1 | 11/2002 | Sun et al. | |
| 2003/0002627 A1 | 1/2003 | Espinosa et al. | |
| 2003/0002628 A1 | 1/2003 | Wilson et al. | |
| 2003/0102222 A1 | 6/2003 | Zhou et al. | |
| 2004/0028183 A1 | 2/2004 | Lu et al. | |
| 2004/0036402 A1 | 2/2004 | Keesmann et al. | |
| 2004/0108298 A1 | 6/2004 | Gao | |
| 2004/0114721 A1 | 6/2004 | Qiu et al. | |
| 2004/0213378 A1 | 10/2004 | Zhou et al. | |
| 2004/0240616 A1 | 12/2004 | Qiu et al. | |
| 2004/0256975 A1 | 12/2004 | Gao et al. | |
| 2005/0133372 A1 | 6/2005 | Zhou et al. | |
| 2005/0226371 A1 | 10/2005 | Kautzer et al. | |
| 2005/0226375 A1 | 10/2005 | Eberhard et al. | |
| 2005/0269559 A1 | 12/2005 | Zhou et al. | |
| 2005/0281379 A1 | 12/2005 | Qiu et al. | |
| 2005/0285541 A1 | 12/2005 | LeChevalier | |
| 2006/0067473 A1 | 3/2006 | Eberhard et al. | |
| 2007/0009081 A1 | 1/2007 | Zhou et al. | |
| 2007/0009088 A1 | 1/2007 | Edic et al. | |
| 2008/0219567 A1 | 9/2008 | Claus et al. | |
| 2008/0240343 A1 | 10/2008 | Jabri et al. | |
| 2009/0022264 A1 | 1/2009 | Zhou et al. | |
| 2009/0041201 A1 | 2/2009 | Wang et al. | |
| 2009/0116617 A1 | 5/2009 | Mastronardi et al. | |
| 2010/0034450 A1 | 2/2010 | Mertelmeier | |
| 2010/0063410 A1 | 3/2010 | Avila | |
| 2013/0294666 A1 | 11/2013 | Bultema | |
| 2014/0221824 A1* | 8/2014 | Rai | A61B 6/12 600/424 |
| 2015/0230768 A1 | 8/2015 | Belei | |
| 2015/0359504 A1 | 12/2015 | Zhou et al. | |
| 2016/0106382 A1* | 4/2016 | Lu | A61B 6/482 600/428 |
| 2016/0193482 A1 | 7/2016 | Fahrig et al. | |
| 2016/0317107 A1 | 11/2016 | Zhou et al. | |
| 2016/0325835 A1 | 11/2016 | Abuelsaad et al. | |
| 2017/0085867 A1 | 3/2017 | Baran et al. | |
| 2017/0329037 A1 | 11/2017 | Zhou et al. | |

FOREIGN PATENT DOCUMENTS

| | | |
|---|---|---|
| CN | 1316279 A | 10/2001 |
| CN | 2462856 Y | 12/2001 |
| CN | 1589744 A | 3/2005 |
| CN | 1672637 A | 9/2005 |
| CN | 1768707 A | 5/2006 |
| CN | 1919372 A | 2/2007 |
| CN | 101641589 A | 2/2010 |
| CN | 101842052 | 9/2010 |
| CN | 101296658 B | 1/2011 |
| CN | 101960333 A | 1/2011 |
| CN | 102551783 A | 7/2012 |
| CN | 102579061 A | 7/2012 |
| CN | 105411620 A | 3/2016 |
| DE | 10164315 A1 | 8/2002 |
| DE | 10164318 A1 | 8/2002 |
| EP | 0 268 488 | 5/1988 |
| EP | 0 648 468 A1 | 4/1995 |
| EP | 1 050 272 A1 | 11/2000 |
| GB | 679617 | 9/1952 |
| JP | 2003100242 A | 4/2003 |
| WO | WO 03/012816 A2 | 2/2003 |
| WO | WO 2004/061477 | 7/2004 |
| WO | WO 2006/116365 A2 | 11/2006 |
| WO | WO 2009/067394 A2 | 5/2009 |
| WO | WO 2013/080111 A1 | 6/2013 |

OTHER PUBLICATIONS

Gauntt, D.M., et al., "An automatic and accurate x-ray tube focal spot/grid alignment system for mobile radiography: System description and alignment accuracy," Med. Phys. 37:12, pp. 6402-6410 (2010).

Miao, H., et al., "A phantom-based calibration method for digital x-ray tomosynthesis," J. X-Ray Sci. Technol. 20, pp. 17-29 (2012).

Qian, X., et al., "High resolution stationary digital breast tomosynthesis using distributed carbon nanotube x-ray source array," Med. Phys. 39;4, pp. 2090-2099 (2012).

Shan, J., et al., "Stationary chest tomosynthesis using a CNT x-ray source array," Proc. SPIE Medical Imaging, vol. 8668, pp. 86680E 1-12 (2013).

Svahn, T.M., et al., "Breast tomosynthesis and digital mammography: a comparison of diagnostic accuracy," Br. J. Radiol., 85, pp. e1074-e1082 (2014).

Tingberg, A., "X-ray tomosynthesis: a review of its use for breast and chest imaging," Radiat. Prot. Dosimetry, vol. 139, No. 1-3, pp. 100-107 (2010).

Bentley, M.D. et al., "The Use of Microcomputed Tomography to Study Microvasculature in Small Rodents", Am. J Physiol Regulatory Integrative Comp Physiol, 282, pp. R1267-1279, 2002.

Bonard, et al., "Field emission from single-wall carbon nanotube films," Appl. Phys. Lett., vol. 73, No. 7, pp. 918-920 (Aug. 17, 1998).

Bower, et al., "Synthesis and structure of pristine and alkali-metal-intercalated single-walled carbon nanotubes," Appl. Phys., A 67, pp. 47-52 (1998).

Bower, C. et al., "Fabrication and Field Emission Properties of Carbon Nanotube Cathodes", Mat. Res. Soc. Symp. Proc., vol. 593, pp. 215-220, 2000.

Brock et al., "Hadamard Transform Time-of-Flight Mass Spectrometry," Analytical Chemistry, vol. 70, No. 18, Sep. 15, 1998.

Brodie, et al., "Vacuum Microelectronics," Advance in Electronics and Electron Physics, edited by P.W. Hawkes, vol. 83, pp. 1-106 (1992).

Bushong, S.C., "Radiologic Science for Technologist," Physics, Biology, and Protection, 6th Edition, Mosby, Inc., 1997 (pp. 107-125) (excerpt relating to focusing and thermionic emission).

A.M. Cassell, et al., "Large Scale CVD Synthesis of Single-Walled Carbon Nanotubes," J. Phys. Chem., B 103, pp. 6484-6492 (Jul. 20, 1999).

Charbonnier et al., "Resolution of Field-Emmision X-Ray Sources," Radiology, vol. 117: pp. 165-172 (Oct. 1975).

Cheng et al., "Dynamic radiography using a carbon-nanotube-based field emmision x-ray source," Review of Scientific Instruments, vol. 75, No. 10: pp. 3264-3267 (Oct. 2004).

De Heer, et al., "A Carbon Nanotube Field-Emission Electron Source," Science, vol. 270, pp. 1179-1180 (Nov. 17, 1995).

Feldkamp L.A. et al., "Practical Cone-Beam Algorithm", J. Opt. Soc. Am., 1(a):612-619, 1984.

Gao et al., "Fabrication and Electron Field Emmision Properties of Carbon Nanotube Films by Electrophoretic Deposition," Advanced Materials, vol. 13, No. 23 (2001) pp. 1770-1773.

(56) References Cited

OTHER PUBLICATIONS

Geis, et al., "Diamond emitters fabrication and theory," J. Vac. Sci. Technol. B, vol. 14, No. 3, pp. 2060-2067, May/Jun. 1996.
Groenhuis, et al., "Computerized tomosynthesis of dental tissues," Oral Surg Oral Med Oral Pathol, 1983. 56: p. 206-214.
Hallenbeck, "Clinical Evaluation of the 350-kV Chest Radiography System," Radiology, vol. 117: pp. 1-4 (1974).
Hu, J. et al., "Chemistry and Physics in One Dimension: Synthesis and Properties of Nanowires and Nanotubes", Accounts of Chemical Research, vol. 32, pp. 435-445, 1999.
C. Journet, et al., "Large-scale production of single-walled carbon nanotubes by the electric-arc technique," Nature, vol. 388, pp. 756-760 (Aug. 21, 1997).
Kumar, et al., "Diamond-based field emission flat panel displays," Solid State Technology, vol. 38, pp. 71-74 (May 1995).
Liang Li, et al., "X-ray digital intra-oral tomosynthesis for quasi-three-dimensional imaging: system, reconstruction algorithm, and experiments," Optical Engineering, 2013. 52(1): p. 013201.
Moore et al., "Three-Dimensional X-Ray Laminography as a Tool for Detection and Characterization of BGA Package Defects", IEEE Transactions on Components and Packaging Technologies. vol. 25, No. 2, Jun. 2002.
Okano, et al., "Electron emission from nitrogen-doped pyramidal-shape diamond and its battery operation," Appl. Phys. Lett., vol. 70, No. 16, pp. 2201-2203 (Apr. 21, 1997).
Okano, et al., "Fabrication of a diamond field emitter array," Appl. Phys. Lett., vol. 64, No. 20, pp. 2742-2744 (May 16, 1994).
Okazaki, et al., "A New Emission Spectrum of Au2 in the Gas Evaporation Technique: 761-809 nm," Jpn. J. Appl. Phys., vol. 37, Pt. 1, No. 1, pp. 349-350 (Jan. 1998).
Resat et al., "Microbeam developments and applications: A low linear energy transfer perspective," Cancer and Metastasis Reviews 23: p. 323-331 (2004).
Ribbing et al., "Diamond membrane based sructures for miniature X-ray sources," Diamond and Related Materials, vol. 11: pp. 1-7 (2002).
Rinzler, et al., "Unraveling Nanotubes: Field Emission from an Atomic Wire," Science, vol. 269, pp. 1550-1553 (Sep. 15, 1995).
Saito, Y. et al., "Field Emission Patterns from Single-Walled Carbon Nanotubes", Jpn. J. Appl. Phys., vol. 36, pp. L1340-L1342. Part 2, No. 10A, Oct. 1, 1997.
Saito, Y. et al., "Cathode Ray Tube Lighting Elements with Carbon Nanotube Field Emitters", Jpn. J. Appl. Phys., vol. 37, pp. L346-L348, Part 2, No. 3B, Mar. 15, 1998.
Slatkin, D et al., Proc. Natl. Acac. Sci. USA, vol. 92, pp. 8783-8787, 1995.
Sloane, "Multiplexing Methods in Spectroscopy," Mathematics Magazine, vol. 52, No. 2 (Mar. 1979), 71-80.
Tang, et al., "Electronic Structures of Single-Walled Carbon Nanotubes Determined by NMR," Science, vol. 288, pp. 492-494 (Apr. 21, 2000).
Thess, et al., "Crystalline Ropes of Metallic Carbon Nanotubes," Science, vol. 273, pp. 483-487 (Jul. 26, 1996).
Traedo, "A Thousand Points of Light: The Hadamard Transform in Chemical Analysis and Instrumentation," Analytical Chemistry. vol. 61, No. 11, Jun. 1, 1989
Vogel et al., "A New Method of Multiplanar Emission Tomography Using a Seven Pinhole Collimator and an Anger Scintillation Camera," Jour. Nuclear Medicine, vol. 19, No. 6, pp. 648-654, 1978.
Wang, et al., "Field emission from nanotube bundle emitters at low fields," Appl. Phys. Leff., vol. 70, No. 24, pp. 3308-3310 (Jun. 16, 1997).
Wang, et al., "A nanotube-based field-emission flat panel display," Appl. Phys. Lett., vol. 72, No. 2, pp. 2912-2913 (Jun. 1, 1998).
Webber, et al., "Comparison of film, direct digital, and tuned-aperture computed tomography images to identify the location of crestal defects around endosseous titanium implants," Oral Surg Oral Med Oral Pathol Oral Radiol Endod 1996. 81: p. 480-490.
Webber, et al., "Hand-held three-dimensional dental x-ray system: technical description and preliminary results." Dentomaxillofacial Radiology, 2002. 31: p. 240.
Weinstein et al., "Data Transmission by Frequency-Division Multiplexing Using the Discrete Fourier Transform," IEEE Trans. on Commun. Tech., vol. Com-19, No. 5, pp. 628-634, Oct. 1971.
Yagishita, et al., "Effects of Cleavage on Local Cross-Sectional Stress Distribution in Trench Isolation Structure," Jpn. J. Appl. Phys., vol. 36, pp. 1335-1340 (Mar. 1997).
Yue et al., "Generation of continuous and pulsed diagnostic imaging x-ray radiation using a carbon nontube based field emission cathode," Applied Physics Letters, vol. 81, No. 2: pp. 355-357 (F) Jul. 8, 2002.
Zhang et al., "Multiplexing radiography using a carbon nanotube based x-ray source," Applied Physics Letters, vol. 89, Aug. 2006.
Zhang et al., "Stationary scanning x-ray source based on carbon nanotube field emitters," Applied Physics Letters, vol. 86, 2005.
Zhou et al., "Materials Science of Carbon Nanotubes: Fabrication, Integration, and Properties of Macroscopic Structures of Carbon Nanotubes", Acc. Chem. Res., vol. 35, pp. 1045-1053, 2002.
Zhu, et al., "Large Current Density from Carbon Nanotube Filed Emitters," Appl. Phys. Lett., American Institute of Physics, vol. 75, No. 6, Aug. 9, 1999, pp. 873-875.
Zhu, et al., "Low-Field Electron Emission from Updoped Nanostructured Diamond," Science, vol. 282, 1471-1473 (Nov. 20, 1998).
Ziegler, et al., "Digital tomosynthesis—experiences with a new imaging device for the dental field," Clin Oral Invest, 2003. 7: p. 41-45.
International Search Report and Written Opinion for PCT Application No. PCT/US08/70477 dated Oct. 1, 2008.
Non-Final Office Action for U.S. Appl. No. 12/176,056 dated Sep. 2, 2009.
First Office Action from Chinese Patent Office for Chinese Patent Application Serial No. 200680013859.X dated Sep. 25, 2009.
Notice of Allowance for U.S. Appl. No. 12/176,056 dated Apr. 2, 2010.
Second Office Action corresponding to Chinese Patent Application No. 200680013859 dated Apr. 30, 2010.
First Office Action for CN Appl. No. 200880107680.X dated Apr. 7, 2011.
Chinese Office Action for Application No. 200880107680.X dated Jan. 14, 2013.
Chinese Notice of Grant for Application No. 200880107680.X dated Aug. 6, 2013.
Non-Final Office Action for U.S. Appl. No. 14/741,041 dated Aug. 18, 2016.
Non-Final Office Action for U.S. Appl. No. 15/205,787 dated May 19, 2017.
Final Office Action for U.S. Appl. No. 14/741,041 dated Apr. 26, 2017.
Notice of Allowance for U.S. Appl. No. 14/741,041 dated Jul. 17, 2017.
German Office Action for German Application No. 112008001902 dated Sep. 15, 2017.
Final Office Action for U.S. Appl. No. 15/205,787 dated Oct. 25, 2017.
Notice of Allowance for U.S. Appl. No. 15/205,787 dated Jan. 3, 2018.
Non-Final Office Action for U.S. Appl. No. 14/886,842 dated Jun. 10, 2019.
Notice of Allowance for U.S. Appl. No. 15/587,052 dated Sep. 13, 2019.
Final Office Action for U.S. Appl. No. 14/886,842 dated Oct. 23, 2019.
Chinese Office Action for Application No. 201510916422.8 dated Nov. 21, 2019.
Chinese Office Action for Application No. 201510450909.1 dated Feb. 3, 2020.
Chinese Office Action for Application No. 201510450909.1 dated Jun. 5, 2020.
Non-Final Office Action for U.S. Appl. No. 14/886,842 dated Jul. 29, 2020.

(56) References Cited

OTHER PUBLICATIONS

Chinese Office Action for Application No. 201510916422.8 dated Aug. 13, 2020.

\* cited by examiner

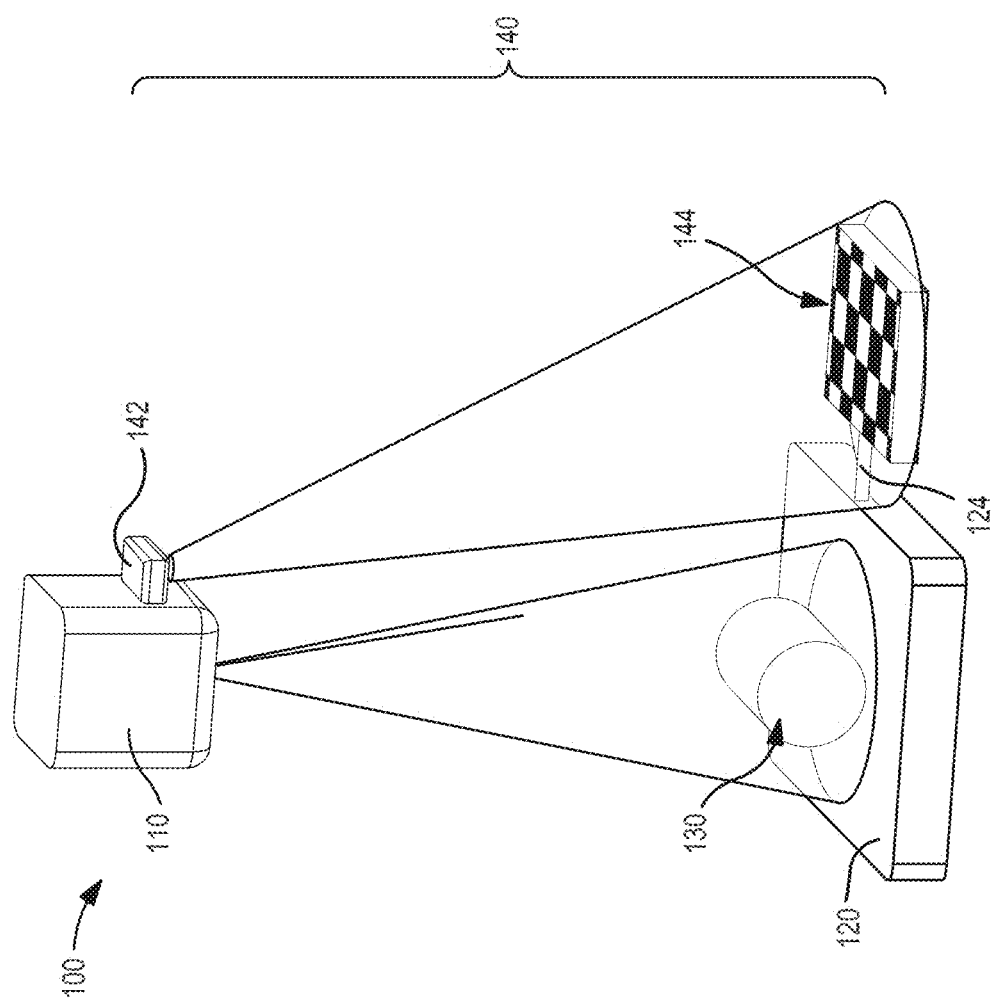

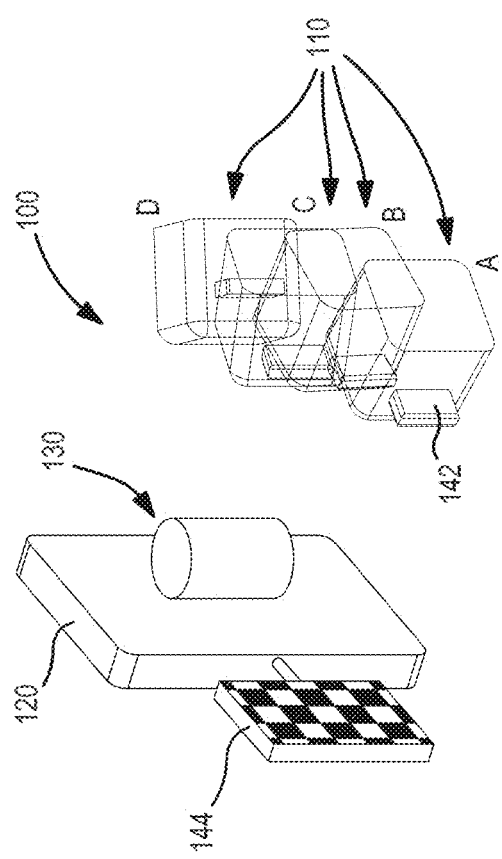
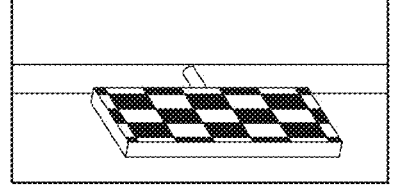
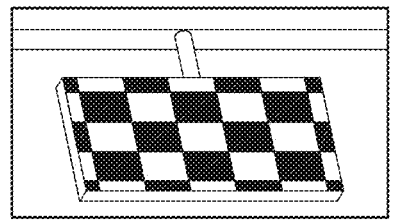
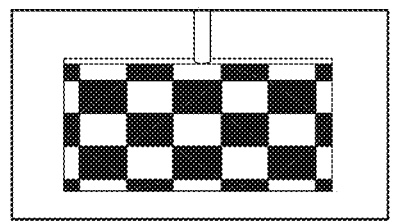
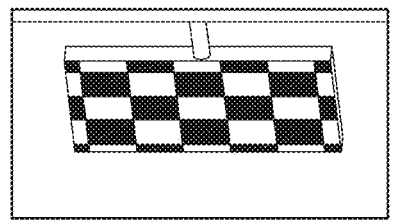

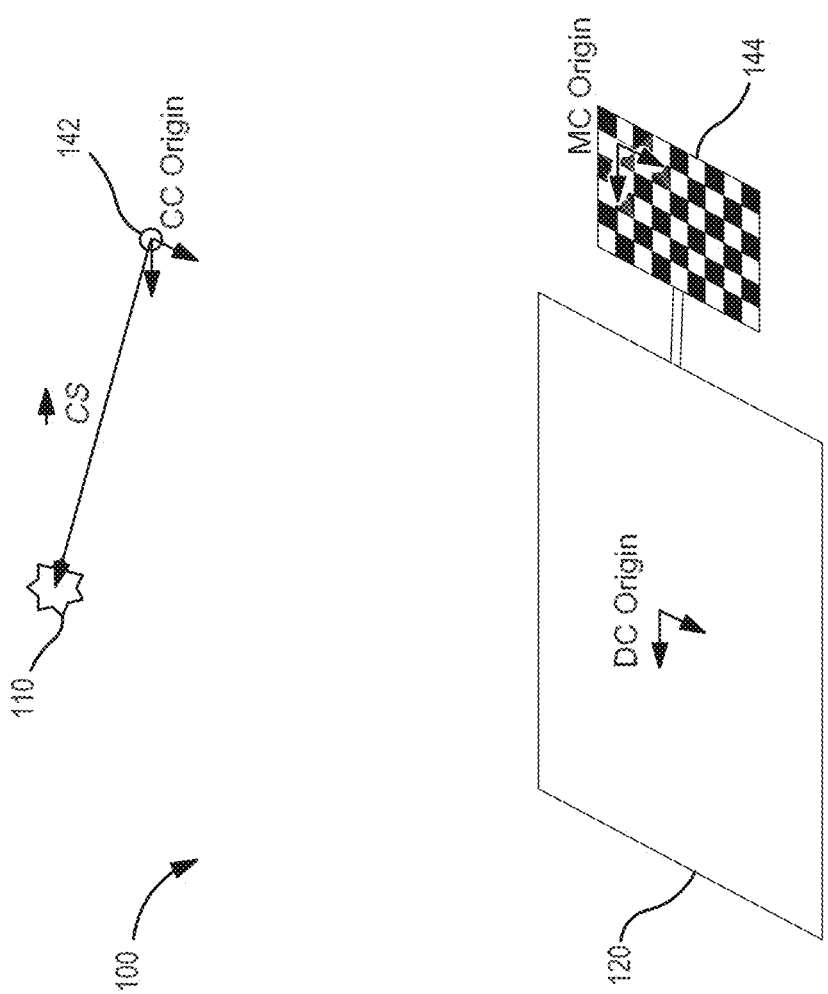

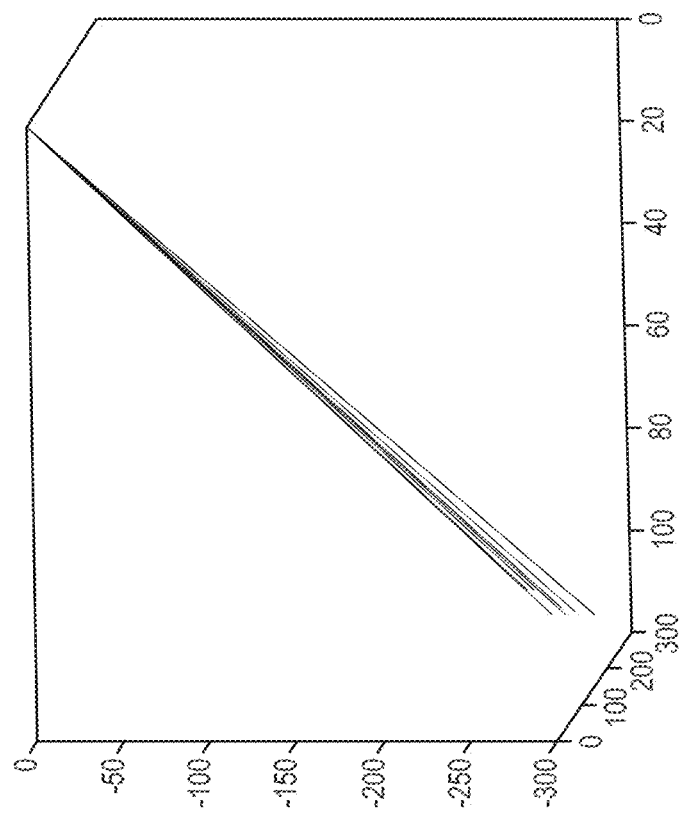
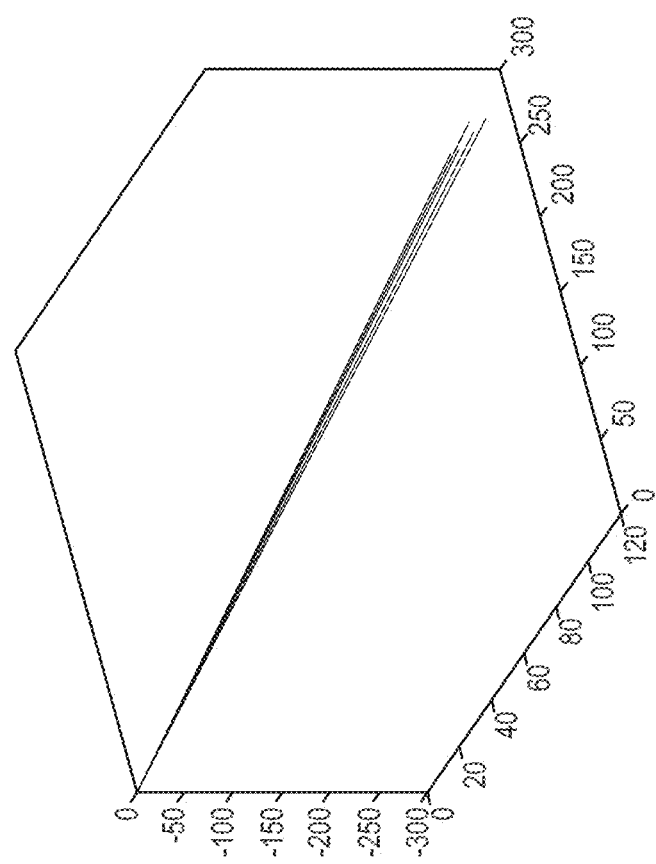
FIG. 8B
FIG. 8A

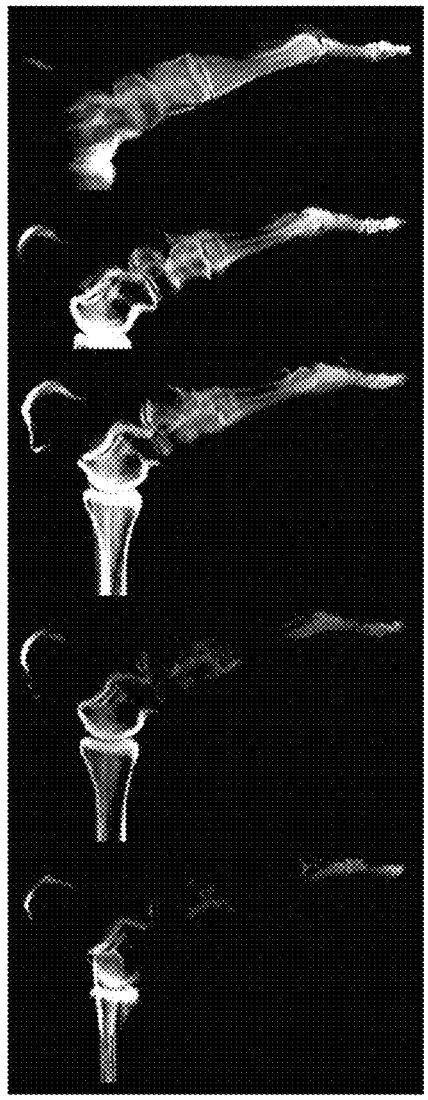
FIG. 15
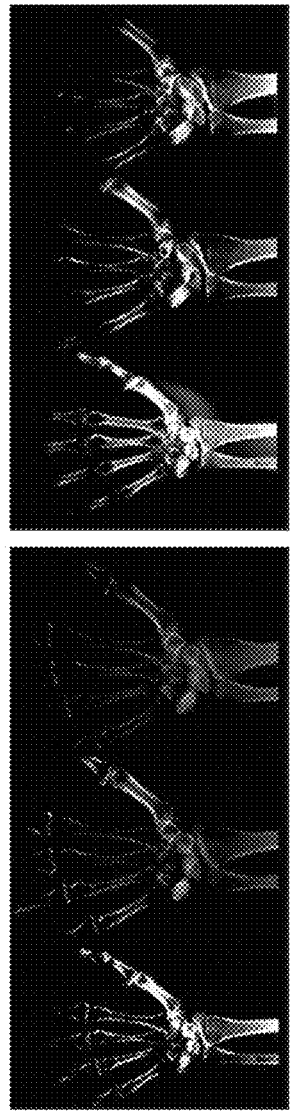
FIG. 16A
FIG. 16B

OPTICAL GEOMETRY CALIBRATION DEVICES, SYSTEMS, AND RELATED METHODS FOR THREE DIMENSIONAL X-RAY IMAGING

PRIORITY CLAIM

The present application claims the benefit of U.S. Patent Application Ser. No. 62/289,714, filed Feb. 1, 2016, the disclosure of which is incorporated herein by reference in its entirety.

TECHNICAL FIELD

The subject matter described herein relates to x-ray radiography and tomography. More specifically, the subject matter disclosed herein relates to calibration devices, systems, and related methods for tomosynthesis imaging.

BACKGROUND

Digital tomosynthesis is a type of limited angle tomography that allows for three-dimensional (3D) information reconstructed from a set of x-ray projection images taken at various angles. Tomosynthesis provides capabilities for filtering out unwanted structure overlap and focusing on a specific slice in an object. Such clinical applications for tomosynthesis include breast cancer screening and diagnosis, imaging of lung diseases, musculoskeletal imaging, etc.

Modern tomosynthesis tubes use typically a traditional x-ray tube, a mechanical arm to move the tube across an angular span, a digital detector, and an x-ray tomosynthesis reconstruction algorithm that provides depth dependent x-ray images. In some aspects, digital tomosynthesis methods range from step and shoot methods that move and stop at each angle to obtain a projection, continuous motion methods that capture images at each angle with the tube in continuous motion while capturing images, and more recent stationary tomosynthesis methods that use a distributed source array to fire x-rays in succession.

Once the images are acquired, x-ray tomosynthesis reconstruction requires knowledge of precise locations of an x-ray source and an x-ray detector with respect to the object being imaged for each projection view taken. In current commercial tomosynthesis scanners, this is accomplished by moving an x-ray source in a fixed and repeatable trajectory and in precise and predetermined angular steps, using a rigid and mechanically stable gantry. Geometry calibration is then performed periodically through imaging a phantom typically composed of multiple x-ray attenuating objects.

While the process works reasonably well for systems stationed in dedicated spaces, it becomes cumbersome and often impractical for mobile and field operations. The heavy mechanical gantry needed for mechanical stability takes up space and makes it difficult to design mobile tomosynthesis scanners that can be useful in situations where the patient cannot be easily transferred, such as those with neck trauma or severe burns. Additionally, a fixed trajectory limits the imaging to simple acquisition geometry such as linear or circular arc acquisition due to practical engineering constraints, which may not provide the most efficient projection image set.

In light of these issues, methods have been developed to accommodate imaging with a non-fixed detector. In a motor control method of tube alignment, for example, a tube head has a six degree of freedom motor system that performs minor adjustments to the tube position after approximate alignment by the technician. The alignment software looks at a protruding cross shape with LEDs and a shape from a camera point of view determines necessary adjustments to be directly above the center of the detector. Other methods include using light patterns to position the detector in a predetermined orientation. However, each of these methods attempt to position a detector at a specific orientation relative to a source, which may be impractical, inconvenient, etc., as multiple orientations during imaging (e.g., for each projection image) may be required.

Accordingly, a need exists for optical geometry calibration devices, systems, and related methods for tomosynthesis imaging that may not only determine source locations for image reconstruction, but may also detect any motion during imaging and still reconstruct images.

SUMMARY

It is an object of the presently disclosed subject matter to provide optical geometry calibration devices, systems, and related methods for x-ray imaging. In particular, systems, devices, and methods disclosed herein can perform tomosynthesis imaging using a decoupled source and detector without a rigid gantry or a predetermined source-detector trajectory. For example, an optical pattern recognition based method to accurately determine the imaging geometries of each projection image, in real time, for tomosynthesis reconstruction that can potentially allow tomosynthesis imaging to be performed using a conventional two-dimensional (2D) imaging system with flexible and variable imaging geometry, is provided.

In some aspects, an imaging system includes an in situ real time determination of imaging geometries by which individual two-dimensional (2D) x-ray projection images are captured for three-dimensional (3D) image reconstruction. The imaging system can include an x-ray source; a detector positioned relative to the x-ray source, the detector being configured to obtain the individual 2D x-ray projection images of an object from a plurality of spatial positions and orientations of the x-ray source and/or the detector relative to the object; an optical-based in situ real time geometry calibration device to determine a spatial position and orientation of the x-ray source and the detector relative to the object for each of the individual 2D x-ray projection images; and an image processing system computing software package configured to reconstruct a 3D structure of the object from the individual 2D x-ray projection images and associated imaging geometry parameters.

In other aspects, a free-form x-ray imaging system for three-dimensional (3D) imaging of an object is disclosed, wherein an x-ray source is freely positioned on one side of the object for emitting x-ray photons. An x-ray detector is mechanically detached from the x-ray source and freely positioned substantially opposite from the x-ray source, the x-ray detector being configured to detect the x-ray photons emitted by the x-ray source. An image processing system is configured to determine a position of the x-ray source and the detector relative to the object being imaged for each projection image and to reconstruct a 3D structure of the object from the projection image and corresponding determined geometry parameters, and a control unit is configured to coordinate an activation of one or more of the x-ray source or the one or more optical cameras.

In further aspects, an optical-based geometry calibration device is configured to interface with a two-dimensional (2D) imaging device to perform three-dimensional (3D) imaging. The optical-based geometry calibration device includes one or more optical cameras fixed to either an x-ray source or an x-ray detector, one or more markers fixed to the x-ray detector or the x-ray source, with each of the one or more optical cameras being configured to capture at least one photographic image of one or more corresponding optical markers when each x-ray image of the object is captured, and an image processing system configured to compute positions of the x-ray source relative to the x-ray detector for each 2D projection image based on the at least one photographic image of the one or more markers.

In other aspects, a method described herein using optical information to determine a source to detector distance and positioning at any location and at any point during the imaging process can be implemented, for example, for a small and versatile imaging system that uses a freestanding detector and either a single x-ray source or a source array without a large and rigid gantry. In some embodiments, the method can include positioning one or more optical marker relative to an x-ray detector and one or more optical camera relative to an x-ray source with predetermined position and orientation, moving the x-ray source and/or the x-ray detector into different positions relative the object being imaged, simultaneously capturing optical images of the one or more marker by the one or more optical camera and obtaining individual two-dimensional (2D) x-ray projection images of the object from a plurality of spatial positions and orientations of the x-ray source and/or the detector relative to the object, using the optical image of the marker to perform in situ real time geometry calibration to determine a spatial position and orientation of the x-ray source and the x-ray detector relative to the object, for each of the individual 2D x-ray projection images, and performing 3D image reconstruction of the object using the 2D x-ray projection images and associated geometry parameters. Used together, the subject matter disclosed herein may not only determine the source locations for reconstruction, but may also detect any motion during imaging and potentially still be able to reconstruct the images as every position for each image is known.

The subject matter disclosed herein can be implemented in software in combination with hardware and/or firmware. For example, the subject matter described herein can be implemented in software executed by a processor. In one example implementation, the subject matter described herein can be implemented using a computer readable medium having stored thereon computer executable instructions that when executed by a processor of a computer control the computer to perform steps. Example computer readable mediums suitable for implementing the subject matter described herein include non-transitory devices, such as disk memory devices, chip memory devices, programmable logic devices, and application specific integrated circuits. In addition, a computer readable medium that implements the subject matter described herein can be located on a single device or computing platform or can be distributed across multiple devices or computing platforms.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described herein below.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which:

FIG. 1 is a schematic illustration of an example free-form 3D imaging system setup including a camera and a source attachment with a pattern attached to a detector according to some embodiments of the subject matter described herein;

FIG. 2 illustrates example camera and/or source motion at four distinct orientations relative to a detector and/or pattern according to some embodiments of the subject matter described herein;

FIGS. 3A-3D illustrate example camera views of optical marker 144 at one of the orientations illustrated in FIG. 2;

FIG. 7 is a schematic illustration of three example coordinate systems relative to an optical geometry calibration system according to some embodiments of the subject matter described herein;

FIGS. 8A-8B illustrate two example views of source to camera vector lines plotted in an example coordinate system according to some embodiments of the subject matter described herein;

FIG. 15 illustrates example screen shots of five slices of a foot phantom using a free-form tomosynthesis imaging setup where an x-ray source was manually moved through 11 distinct positions relative to the foot phantom across an approximately 15 degree arc according to some embodiments of the subject matter described herein; and FIGS. 16A-16B illustrate example screen shots of three slices of a hand phantom from two different depths using a free-form tomosynthesis imaging setup according to some embodiments of the subject matter described herein.

DETAILED DESCRIPTION

Figure 4:
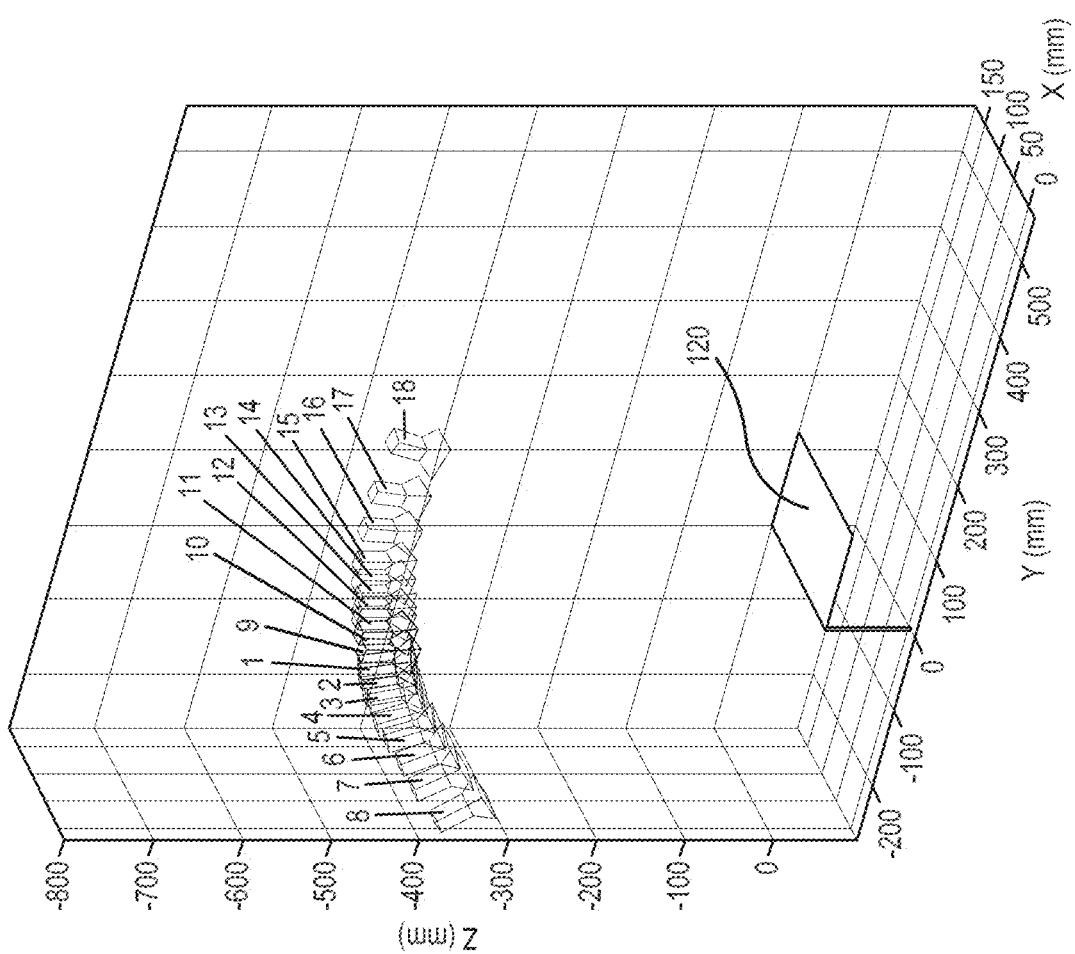
FIG. 4 illustrates a three-dimensional (3D) plot of camera and source positions (numbered dots) relative to a detector according to some embodiments of the subject matter described herein.

The present subject matter relates to optical geometry calibration devices, systems, and related methods for tomosynthesis imaging.

As used herein, the terms "patient", "human", "subject", and "object" are used generically to mean an entity that is being scanned by a tomosynthesis imaging device, apparatus, system, etc., unless otherwise specified.

In a traditional tomosynthesis imaging device, system, apparatus, assembly, setup, etc., a position of an x-ray detector relative to x-ray source(s) is always known due to prior calibrations and its fixed position(s), such that geometry of the detector relative to the source(s) does not need to be determined for each data acquisition. By contrast, in a free-form setup for a tomosynthesis imaging device, system, apparatus, assembly, etc., a detector can be in any position(s) relative to a source(s) and move from image to image, where relative positions of the source(s) with respect to the detector need to be determined for each projection image.

Systems, devices, and methods disclosed herein are able to accomplish such a determination in a free-form setup. In some aspects, x-rays alone may be used. In some embodiments, a phantom is placed on a detector alongside an object being imaged, although such a technique can be difficult to implement if the object is as large as or larger than the detector. In other embodiments, a phantom or other marker is placed on the object, and two images per position may be captured: one for calibration and one for the image set. This second technique avoids the problem of the first x-ray-only technique with respect to oversized objects, but the second x-ray-only technique adds additional radiation. In a further alternative embodiment, however, a pattern of known size is positioned at or near the detector and tracked. The tracking allows for an accurate position of optical marker 144, and the knowledge of optical marker 144's position relative to the detector allows for the calculation of the position of the detector relative to an x-ray source.

FIG. 1 illustrates one aspect or embodiment of an example free-form setup of a 3D imaging system, generally designated 100. As shown in FIG. 1, 3D imaging system 100 includes an x-ray source 110 (e.g., either a single focal spot or multiple distributed focal spots) and a detector 120 (e.g., a flat panel detector or a multi-pixel detector) arranged with respect to each other such that one or more individual 2D x-ray projection images can be acquired of an object, generally designed 130, which is placed between an x-ray source 110 and detector 120. In addition, x-ray source 110 can be movable with respect to detector 120 such that the one or more individual 2D x-ray projection images can be acquired at different positions and/or angles, and a three-dimensional (3D) tomosynthesis image can be constructed from the 2D x-ray projection images. (See, e.g., FIGS. 2 and 4) In particular, as discussed above, x-ray source 110 and detector 120 can be mechanically decoupled from one another such that the 3D imaging system 100 is operable as a free-form setup.

As part of the free-form configuration of 3D imaging system 100, the presently-disclosed subject matter further provides systems, devices, and methods to determine relative positions of the source(s) with respect to the detector for each projection image. In this regard, in addition to the x-ray imaging elements, 3D imaging system 100 can include an in situ, real-time geometry calibration device, generally designated 140, that is configured to determine a spatial position and orientation of x-ray source 110 and detector 120 relative to object 130 for each of the individual 2D x-ray projection images. In some embodiments such as that illustrated in FIG. 1, geometry calibration device 140 includes one or more optical imaging device 142 (e.g., a camera) that is mounted in a substantially fixed position with respect to x-ray source 110. In some aspects, different types of cameras may be used. For example, a LOGITECH® camera may be used and calibrated using software that provides all intrinsic parameters to be used during optical reconstruction. Resolution of optical imaging device 142 may be set to 1920× 1080 with or without auto-focus. In some embodiments, for example, optical imaging device 142 is mounted directly to x-ray source 110 (e.g., to a side of a housing of x-ray source 110) such that optical imaging device 142 does not move relative to x-ray source 110.

Geometry calibration device 140 further includes one or more optical marker 144 positioned in a substantially fixed position with respect to object 130. In particular, for example, in some embodiments where the position of object 130 is substantially fixed with respect to a position of detector 120 (e.g., object 130 is placed on top of detector 120), optical marker 144 can be mounted to detector 120. In the configuration shown in FIG. 1, for example, optical marker 144 is mounted to detector 120 by an extension arm 124 such that optical marker 144 does not move relative to detector 120.

Regardless of the particular configuration and/or relative positioning of the elements of 3D imaging system 100, geometry calibration device 140 is configured to track the relative position of x-ray source 110 with respect to detector 120 and/or object 130. In this regard, in some embodiments, optical marker 144 has a shape and/or design that is designed such that the position and/or orientation of optical marker 144 can be determined based on its appearance as viewed by optical imaging device 142. In other words, one or more characteristics of optical marker 144 can be designed such that they have a distinct appearance depending on the relative angle, position, and/or distance of optical marker 144 with respect to optical imaging device 142. In some embodiments, for example, optical marker 144 comprises a texture or pattern provided on a surface of optical marker 144 (e.g., printed, etched) that faces optical imaging device 142, and optical imaging device 142 is configured to track motion of optical marker 144. In some particular embodiments, for example, optical marker 144 is an optical pattern including a black and white chessboard pattern. (See, e.g., FIGS. 1 and 2) Those having ordinary skill in the art will recognize that checkerboard or chessboard pattern recognition can be used for camera calibration and feature extraction. Alternatively, in some embodiments, optical marker 144 is a geometrical pattern of object 130 itself, wherein the relative position and/or orientation of object 130 is determined based on the appearance of object 130 from the perspective of optical imaging device 142. In any configuration, where optical imaging device 142 is substantially fixed in position with respect to x-ray source 110, and where optical marker is substantially fixed in position with respect to detector 120 and/or object 130, the location of object 130 relative to x-ray source 110 can thereby be determined based on a relative position change.

In this configuration, x-ray source 110 is movable (e.g., manually or mechanically) to any of a range of spatial locations and orientations with respect to detector 120 to acquire the one or more individual 2D x-ray projections of object 130, and geometry calibration device 140 is operable to capture one or more optical images of optical marker 144 at each position where an individual 2D x-ray projection image of object 130 is taken. In this way, the optical images can be used to determine the position of x-ray source 110 relative to detector 120 and/or object 130 based on the orientation of optical imaging device with respect to optical marker 144. FIG. 2 illustrates motion of x-ray source 110 to four distinct orientations (identified as positions A, B, C, and D) relative to detector 120 and/or object 130, while FIGS. 3A-3D each illustrate views of optical marker 144 from optical imaging device 142 at each position provided in FIG. 2. The perception of the rotation and position of optical marker 144 allows for an absolute position calculation to be performed.

By identifying the corresponding geometry parameters in this way based on the perception of optical marker 144 by optical imaging device 142, a 3D structure of object 130 can be reconstructed from the projection images. To accommodate this geometry calibration, optical marker 144 must remain visible to optical imaging device 142 during imaging. Since x-ray source 110 is movable to any of a range of positions with respect to detector 120, in some embodiments, optical imaging device 142 is positioned relative to x-ray source 110 and optical marker 144 is positioned relative to detector 120 and/or object 130 such that optical marker 144 does not become obscured as x-ray source 110 is moved. Referring to FIGS. 1 and 2, for example, optical imaging device 142 can be positioned on a side of x-ray source 110, and optical marker 144 can be positioned on a corresponding side of detector 120 such that optical imaging device 142 can maintain line-of-sight to optical marker 144 as x-ray source 110 is moved relative to detector 120 (e.g., among positions A, B, C, and D shown in FIG. 2).

FIG. 4 illustrates a three-dimensional (3D) representation of positions of optical imaging device 142 and x-ray source 110, identified as positions 1-18, relative to detector 120. In this representation, it is apparent how x-ray source 110 and/or optical imaging device 142 may be manually or mechanically positioned about detector 120. In some embodiments, x-ray source 110 (and optical imaging device 142) can be configured to follow a substantially perfect arc about object 130 (e.g., over a limited angular range). Alternatively, in some embodiments, x-ray source 110 can be moved in any of a variety of non-arcuate movements relative to object 130. Because of the geometric correction provided by geometry calibration device 140, 3D tomosynthesis image reconstruction can be performed regardless of what individual 2D x-ray projection images are captured. In this way, in some embodiments, for example, 3D imaging system 100 enables a reconfigurable and flexible imaging geometry, allowing collection of projection images with variable source-detector distances and flexible source trajectory.

Figure 5:
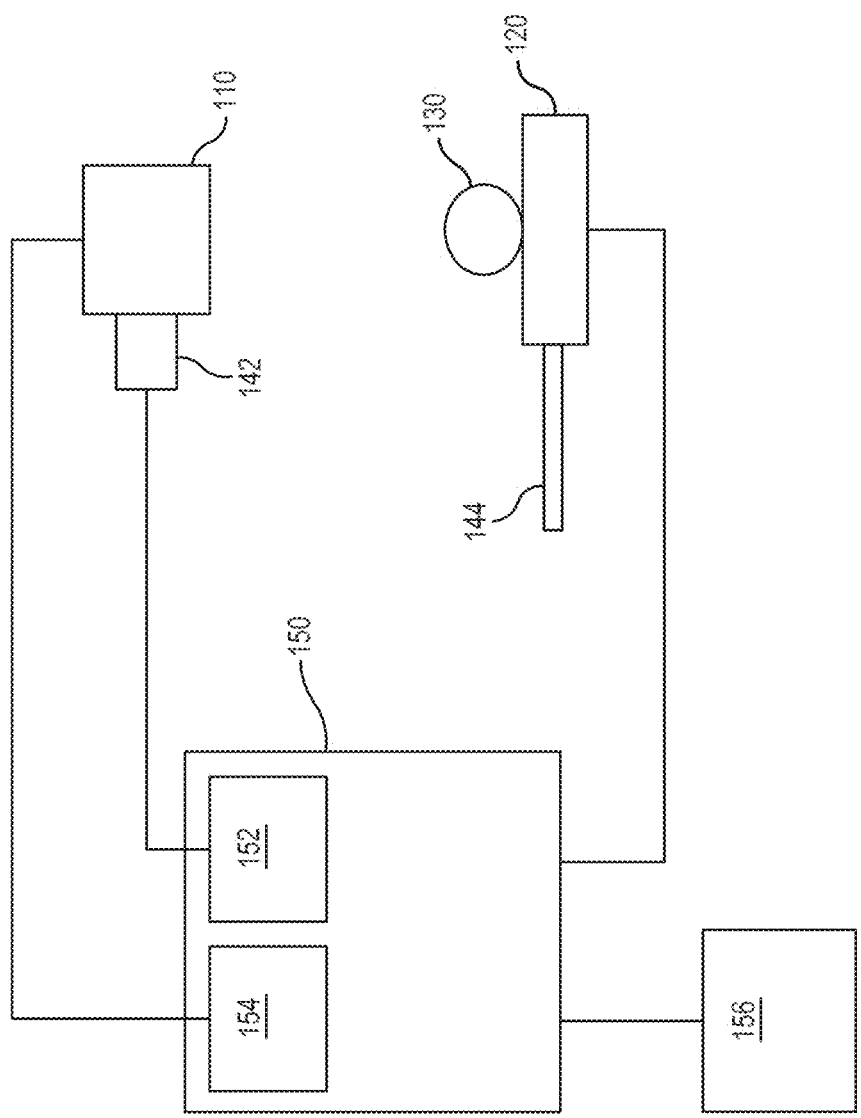
FIG. 5 illustrates a schematic diagram of an image processing and control system for a 3D imaging system according to an embodiment of the subject matter described herein.

In this regard, referring to FIG. 5, in some embodiments, geometry calibration device 140 and detector 120 are both in communication with an image processing system 150 that is configured to reconstruct the 3D structure of object 130 from the individual 2D x-ray projection images and associated imaging geometry parameters. In particular, image processing system 150 can include an optical image processor 152 in communication with optical imaging device 142 that is configured to compute the spatial position and orientation of x-ray source 110 and detector 120 relative to object 130 based on a comparison of the at least one photographic image of optical marker 144 to prior dimensions of optical marker 144, prior relative positions of optical imaging device 142 with respect to x-ray source 110, and a relative position of optical marker 144 with respect to detector 120. In some embodiments, image processing system 150 includes a control unit 154 in communication with one or more components of 3D imaging system 100 (e.g., x-ray source 100, optical imaging device 142) and configured to coordinate the activation of those components. In addition, in some embodiments, a display 156 in communication with image processing system 150 can be configured to display the reconstructed 3D structure of object 130.

Figure 6:
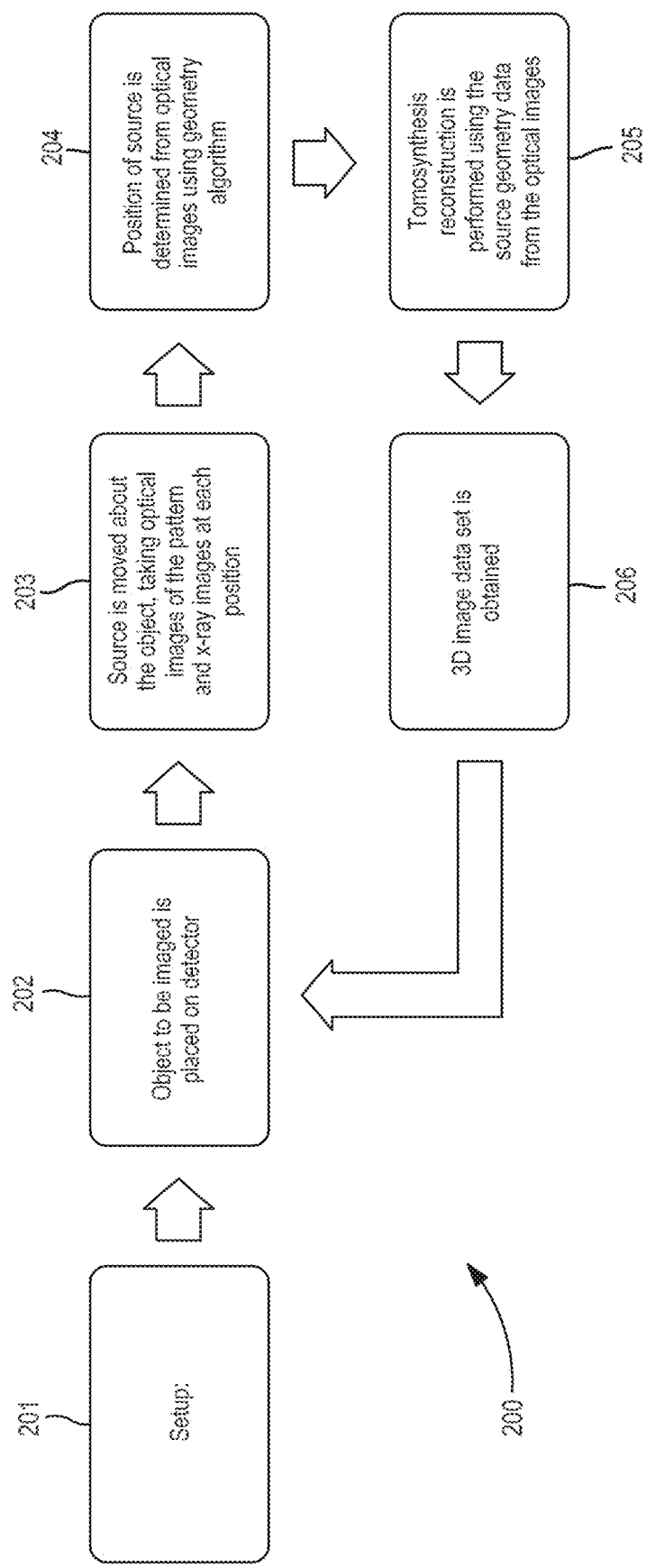
FIG. 6 illustrates a flow chart of an example optical geometry calibration process for tomosynthesis imaging according to some embodiments of the subject matter described herein.

Referring now to FIG. 6, a flow chart illustrating an example optical geometry calibration process for tomosynthesis imaging, generally designated 200, is provided. During an initial setup 201, optical marker 144 (e.g., a checkboard or chessboard pattern) may be mounted on and/or near detector 120, while optical imaging device 142 may be mounted on x-ray source 110. Initial setup 201 can further include accumulating knowledge of the relative position of optical imaging device 142 relative to a focal spot of x-ray source 110 (i.e., initial calibration), which may be utilized to perform the geometry calculation. For example, moving optical imaging device 142 in this manner, in conjunction with a vision library stored in a database related to a computing platform, results in a determination of intrinsic parameters of optical imaging device 142 using a series of calibration images taken of optical marker 144 in various positions and/or rotations.

Following initial setup 201, a system positioning step 202 can include positioning object 130 between x-ray source 110 and detector 120 (e.g., on detector 120). A source sweep step 203 can include moving x-ray source 110 relative to object 130, taking optical images of optical marker 144 and x-ray images of object 130 at each of a plurality of positions. Next, in a geometry calibration step 204, a position of x-ray source is determined from optical images using a geometry calibration algorithm. A reconstruction step 205 can then include performing a tomosynthesis reconstruction using the source geometry data from the optical images. X-ray projection images may be reconstructed using reconstruction software, such as, for example, commercial filtered back projection software, which allows for any source geometry to be input. Finally, an image formation step 206 can include obtaining the 3D image data based on the reconstruction. The steps of optical geometry calibration process 200 can be repeated as needed to generate the desired 3D tomographic images of object 130.

As will be appreciated by those having ordinary skill in the art, the accuracy of the geometric calibration and reconstruction of the 2D projection images can depend on the initial setup 201. As part of the initial imaging calibration, an x-ray-source-to-camera calibration can be performed. First, a standard metal bead calibration phantom that is suited to determine an absolute position of x-ray source 110 to detector 120 for stationary tomosynthesis may be used. The phantom may be placed on detector 120. Next, x-ray source 110 may be moved relative to the calibration phantom, and optical images of optical marker 144 and x-ray images of the phantom may be (simultaneously) taken at different orientations of x-ray source 110 relative to detector 120. Where x-ray source 110 and/or optical imaging device 142 is moved about detector 120 and/or optical marker 144, it may be desirable to ensure that neither component is moved relative to each other, and an x-ray and corresponding optical image of optical marker 144 is taken at each position. Then, a position of x-ray source 110 may be determined from the optical images using a geometry algorithm. In this manner, absolute source focal spot positions relative to detector 120 and the absolute optical focus spot position relative to optical marker 144 may be determined. Since the position of optical marker 144 relative to detector 120 is known, the position of x-ray source 110 can be determined relative to the optical focal spot. Notably, once optical imaging device 142 and/or x-ray source 110 is calibrated, the phantom may no longer be needed as the position of optical marker 144 to optical imaging device 142 can be used to determine the position of x-ray source 110 to detector 120.

Next, tomosynthesis reconstruction can be performed using, for example, the source geometry data from the optical images. For example, the source geometry data from the optical images may be used in tomosynthesis reconstruction software implemented at a computing platform to reconstruct 3D tomosynthesis slice images of the ROI of an object. The images can be reconstructed by using a suitable technique such as filtered back projection (FBP), simultaneous iterative reconstruction technique (SIRT), or model based iterative reconstruction (MBIR), to obtain a 3D tomographic image of the object. For example, the computing platform can comprise a tomosynthesis reconstruction software package utilizing a variety of algorithms including shift-and-add, filtered back projection, ordered subsets convex maximum likelihood, etc.

A more detailed description of calibrating an optical camera is provided in FIG. 7. More particularly, FIG. 7 illustrates three related, but distinct coordinate systems relative to an optical geometry calibration system: a camera coordinate (CC) system that has an origin at a focal spot with Z being a vertical distance away, a detector coordinate (DC) system that has an origin in a middle, with positive X and Y axes being to a right and down, respectively, when looking at the DC system from a top view, and a marker coordinate (MC) system where an origin is at a top left corner intersection of four squares with X and Y axes in a same direction as with a detector. In some aspects, using the intrinsic parameters from the initial calibration, translation and rotation vectors of optical imaging device 142 can be obtained, which relate the CC system and the MC system using the matrix transform:

$$X_{CC} = RX_{MC} + t \tag{1}$$

From this, a position of optical imaging device 142 in the MC system can be obtained:

$$X_{MC} = -R't \tag{2}$$

Next, the DC system may be related to the MC system. As the two are connected, their position can be determined in a number of ways. For example, it may be assumed, where positioning of optical marker 144 is controlled, that the two planes are parallel and their transform is a linear one, with $M_X$, $M_Y$, $M_Z$ being the linear offsets between the DC system and the MC system. The transform can be applied to a randomly rotated and/or translated pattern to a detector plane as well.

$$X_{DC} = X_{PC} - \begin{bmatrix} M_x \\ M_y \\ M_z \end{bmatrix} \tag{3}$$

A final relation is a position of x-ray source 110 with respect to a camera focal spot, after which a position of x-ray source 110 with respect to detector 120 can be obtained from the above transforms. To do so, a calibration phantom may be used to first get a source in the DC system. This is done using a standard geometry calibration phantom and ray tracing.

The calibration is then completed by accurately getting the $\vec{cs}$ vector. From the geometry phantom, the position of x-ray source 110 in the DC system, which, using equation (3), can be determined in the MC system. Using equation (1), this can be substituted back into the CC system. Plotting all of the vectors from the origin (e.g., optical imaging device 142 focal spot) to x-ray source 110 should theoretically all give the same vector, but due to measurement errors, gives slightly different results, shown plotted in FIGS. 8A-8B. Taking the average of those gives the $\vec{cs}$ vector.

Accordingly, in some aspects, once these steps are complete, optical geometry calibration is completed. From the geometry calibration data obtained, any new x-ray projection image and/or corresponding optical image can be processed to determine a position of x-ray source 110 with respect to detector 120. Using the $\vec{cs}$ vector and equation (1), the position of x-ray source 110 in the DC system can be found by equation (4):

$$Source_{DC} = R'\left(\begin{bmatrix} CS_X \\ CS_Y \\ CS_Z \end{bmatrix} - t\right) \tag{4}$$

Figure 9:
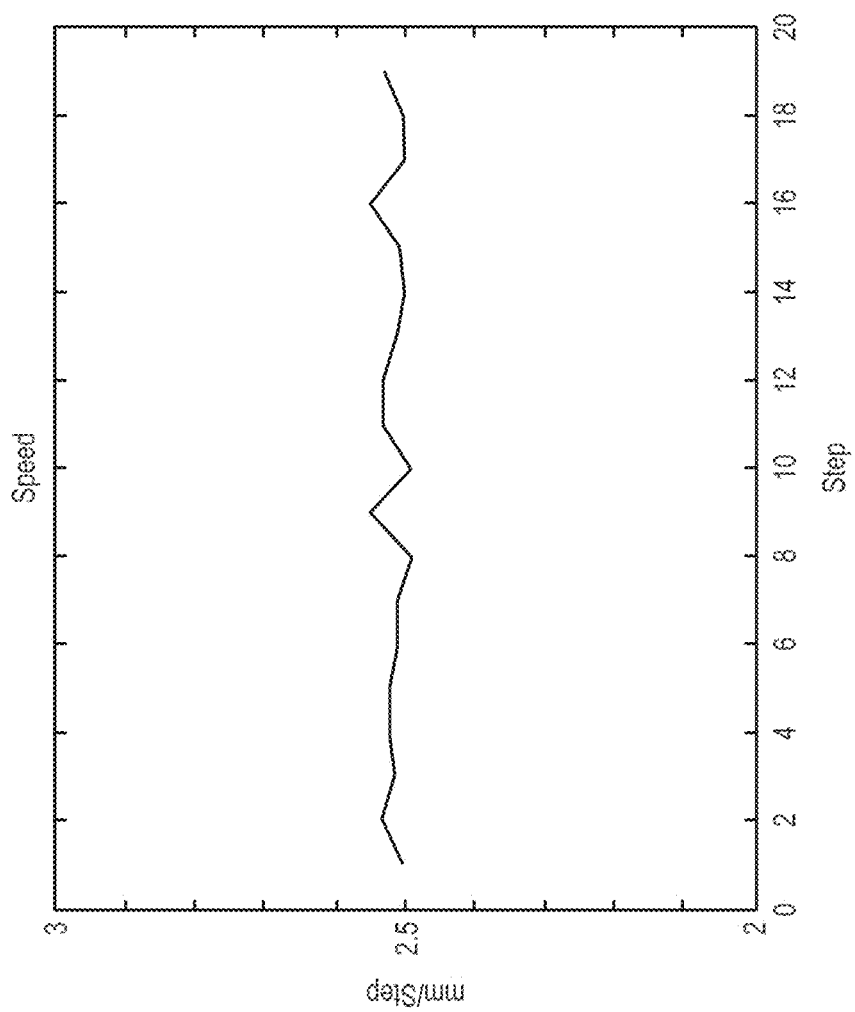
FIG. 9 is a plot illustration of average speed per step in an example optical geometry calibration process for tomosynthesis imaging according to some embodiments of the subject matter described herein.

In some aspects, optical tracking may be tested for accuracy in order to determine a minimum error threshold assuming perfection conditions. For example, a precision translation stage may be used and a camera setup may be moved a known distance in three dimensions. For example, a continuous motion translation motion stage(s) moving at 2.5 mm/s may be used with a camera frame rate set to 1 fps, such that 20 or more images may be taken and the geometry calculated. FIG. 9 illustrates a plot of average speed per step. Then, the known distance(s) may be compared to the ones calculated by the optical geometry calibration devices, systems, and methods.

Figure 10:
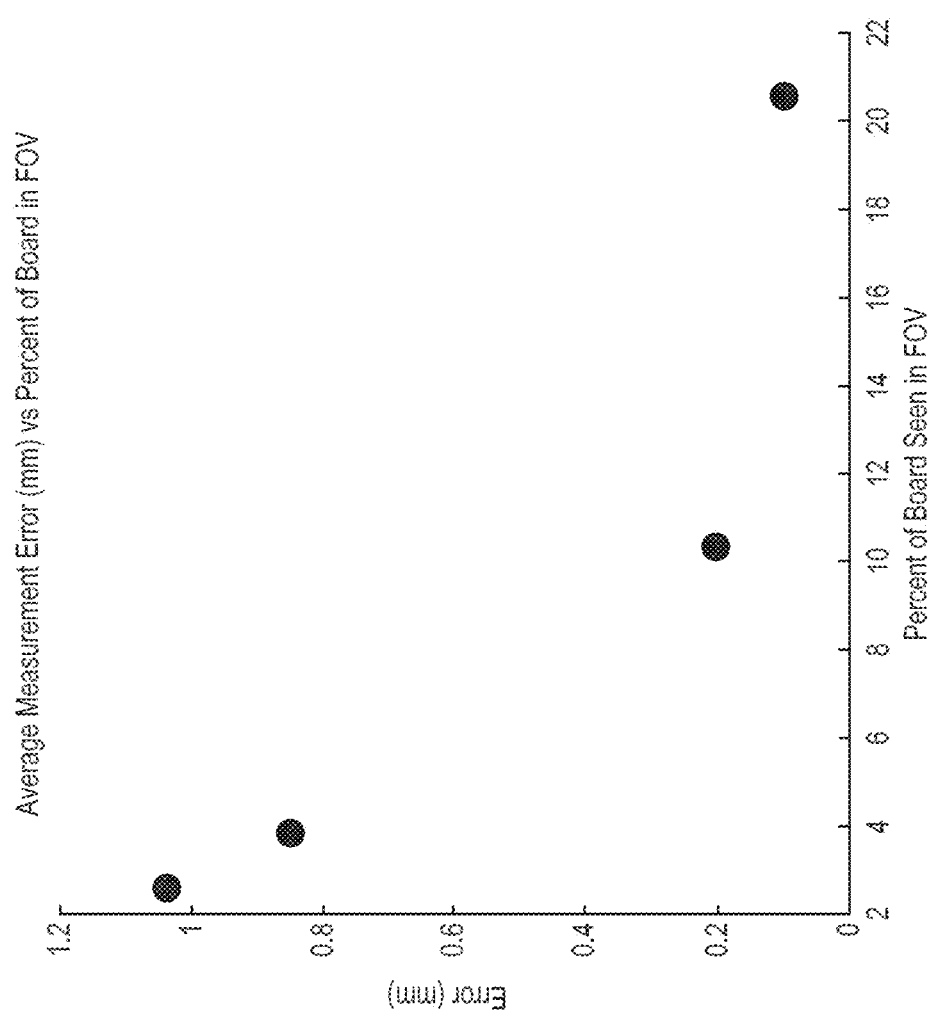
FIG. 10 is a plot illustration of an average measurement error (mm) versus percent of board in a field of view (FOV) of an example optical geometry calibration process for tomosynthesis imaging according to some embodiments of the subject matter described herein.
Figure 11:
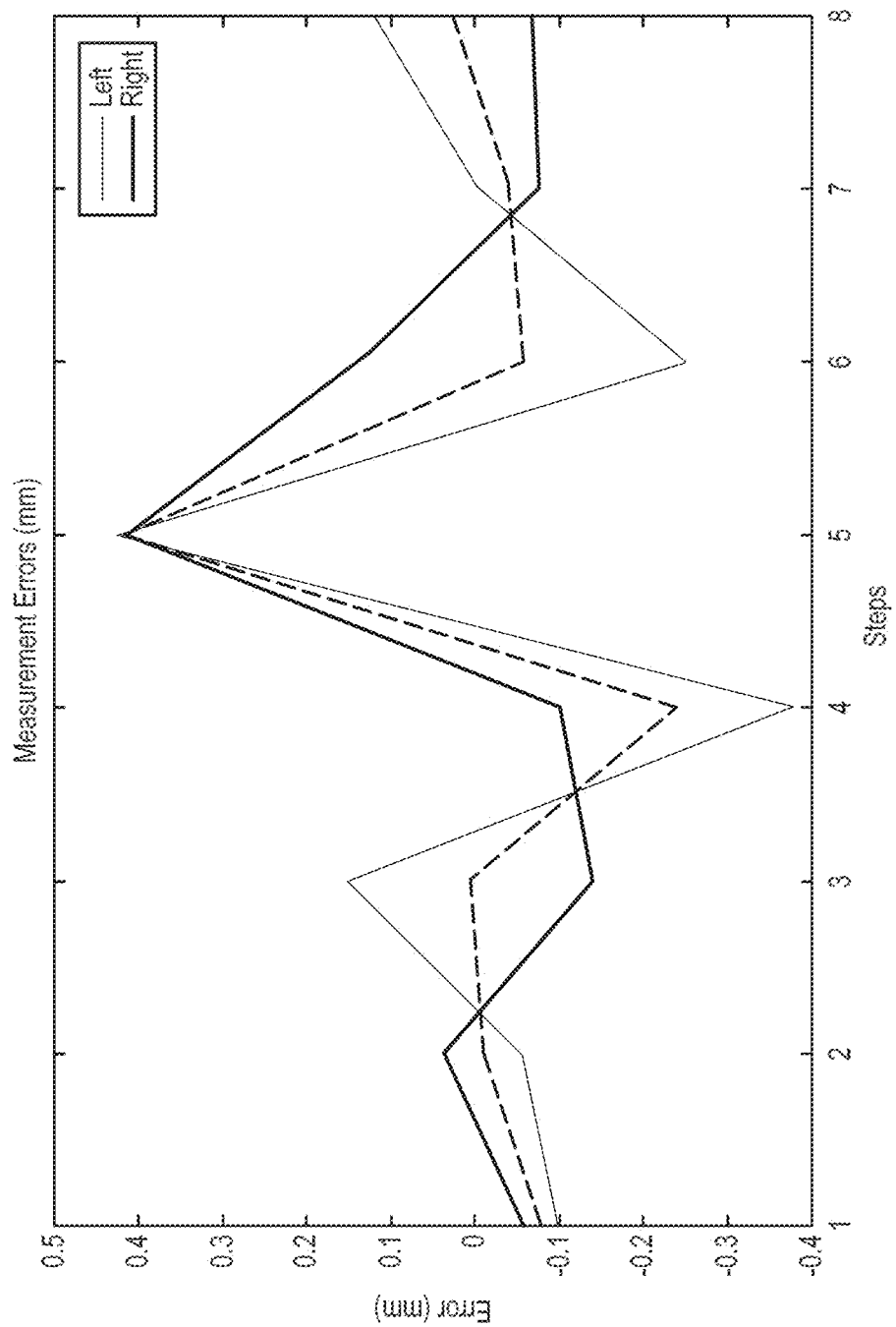
FIG. 11 is a plot illustration of two camera accuracy in the X-Y plane in an example optical geometry calibration process for tomosynthesis imaging according to some embodiments of the subject matter described herein.
Figure 12A:
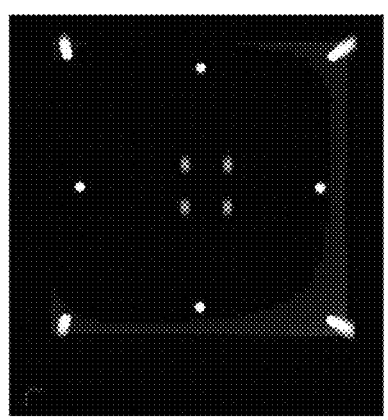
FIGS. 12A-12F illustrate various slices (i.e., 7, 20, 63) of geometry calibration phantom reconstructions using geometry phantom source position data (top) compared to the optically calculated source positions (bottom) showing wire and different beads in focus according to some embodiments of the subject matter described herein.
Figure 12B:
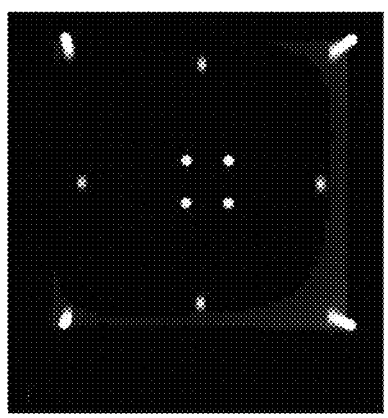
Figure 12C:
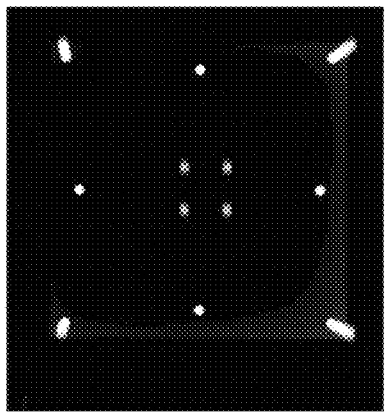
Figure 12D:
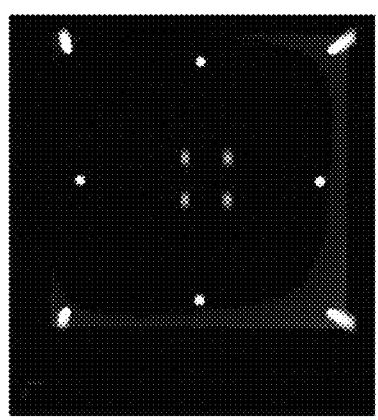
Figure 12E:
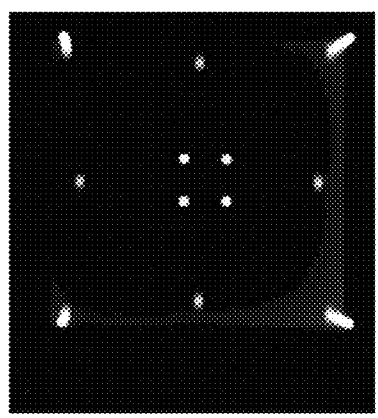
Figure 12F:
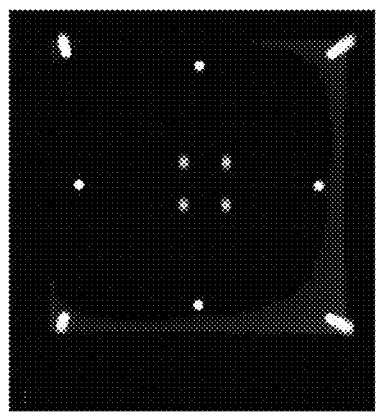
Figure 13A:
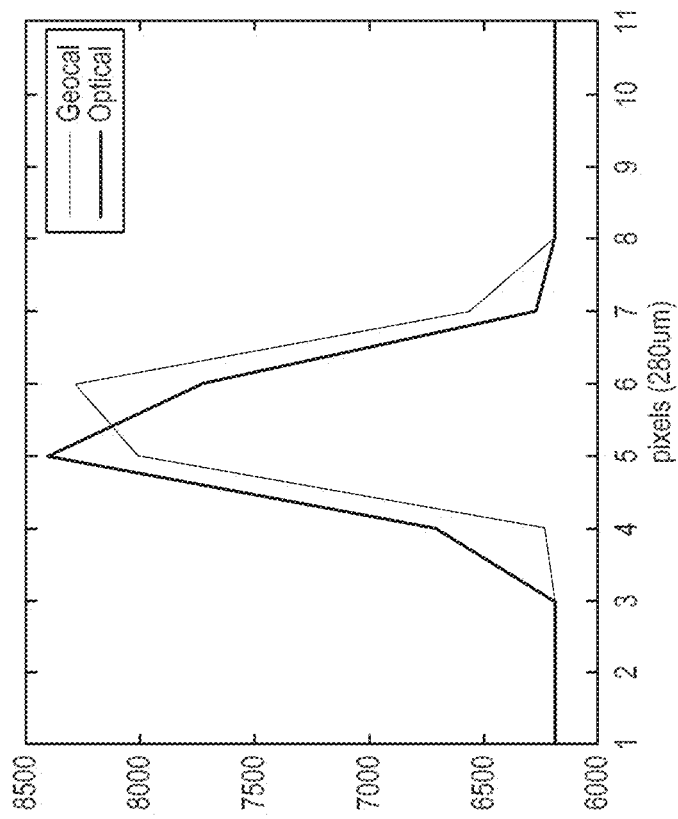
FIGS. 13A-13B illustrate plots of horizontal and vertical profiles, respectively, of the phantom from both reconstructions in FIGS. 12A-12F.
Figure 13B:
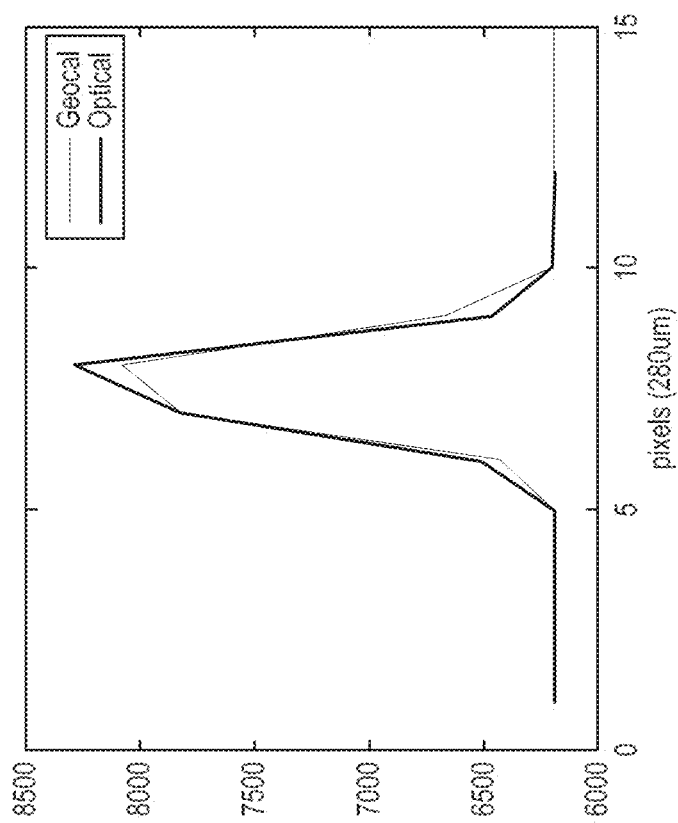

Other conditions affecting accuracy of optical geometry calibration devices, systems, and methods may also be tested for a minimum error threshold, including a distance from optical marker 144, percentage of an image that comprises a pattern, and/or camera resolution. Notably, in some aspects, optimal camera resolution may be 1920×1080, although other resolutions may be considered optimal. For example, higher resolutions may not result in better accuracy and may result in slower acquisition time. In other aspects, a percentage of an image that comprises a pattern, taking into account both the distance and size of optical marker 144 may be desirable to optimize. For example, the larger optical marker 144 appears in the image, the smaller the error. This is illustrated in FIG. 10, where an average measurement error (mm) versus percent of board in a field of view (FOV) was aimed to keep optical marker 144 filling about 20% of the image during imaging. In this manner, two cameras were used to reduce the error, as seen in FIG. 11. An error test in the X-Y plane illustrates an average error of less than 10 microns using both cameras, with a maximum error of approximately 400 μm.

In some additional or alternative aspects, relative positioning may be tested for accuracy by using a calibration phantom as the absolute reference. For example, optical imaging device 142 may be attached to x-ray source 110, and a phantom may be optically and x-ray imaged as optical imaging device 142 and/or x-ray source 110 is moved around it. Motion detected by optical imaging device 142 may be compared to motion obtained from the x-ray projection geometry calculation. Both of the position sets obtained from the x-ray geometry phantom and the optical geometry may be used to reconstruct the calibration phantom. FIGS. 12A-12F illustrates various slices (i.e., 7, 20, 63) of the geometry calibration phantom reconstructions using the geometry phantom source position data (top) compared to the optically calculated source positions (bottom) showing the phantom (i.e., wire and different beads) in focus. In light of the comparison of FIGS. 12A-12C against FIGS. 12D-12F, FIGS. 13A-13B provide for horizontal and vertical profiles of the wire from both reconstructions. The horizontal slice has a thickness of 604 µm versus the actual 635 µm—a 4.9% error for both reconstructions. The vertical profile thicknesses were 566 µm and 547 µm for the calibration phantom and optical respectively—10.8% and 13.9% errors from the actual width and a 3.4% error between the x-ray projection geometry phantom (geocal) and the optically calculated source positions (optical).

Figure 14B:
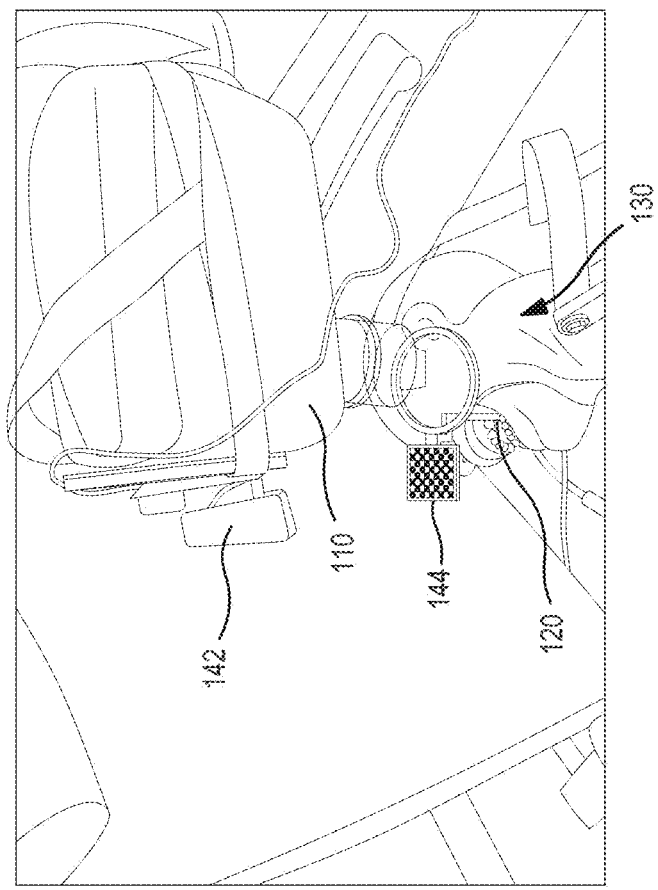
FIGS. 14A-14B illustrate perspective top views of an example oral tomosynthesis imaging system comprising an intraoral detector and a custom holder with an optical pattern according to some embodiments of the subject matter described herein.
Figure 14A:
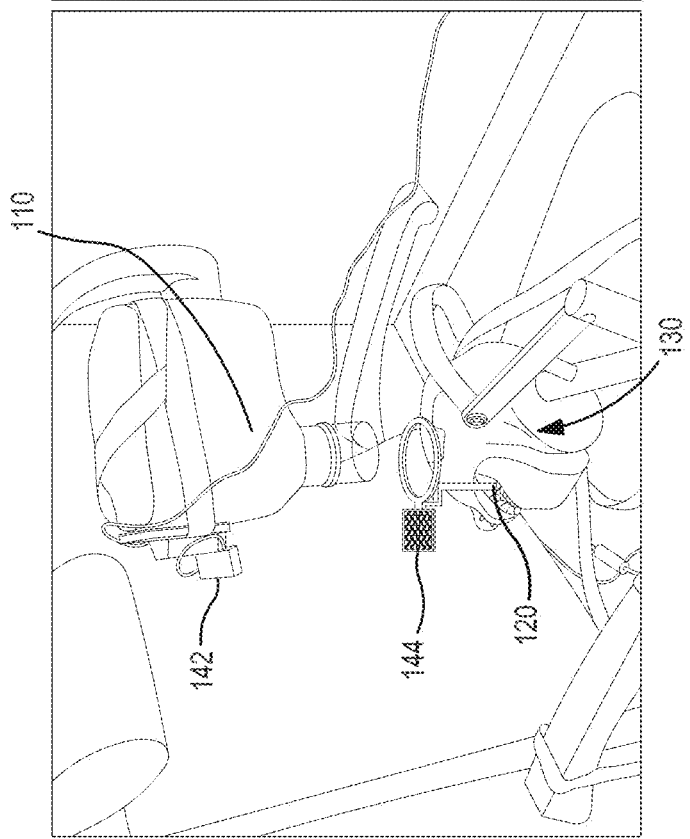

In some aspects, the optical geometry calibration devices, systems, and methods for tomosynthesis imaging may be used in multiple imaging applications, such as intraoral imaging. For example, in FIGS. 14A-14B, an example oral tomosynthesis imaging system comprising an intraoral detector 120 and a custom holder with optical marker 144 is illustrated. Optical geometry calibration using a head phantom (i.e., identified in FIGS. 14A-14B as object 130) with a geometry calibration phantom next to the head phantom in order to compare reconstructions using the absolute geometry from the head phantom and that obtained using the optical imaging method may be used. In this embodiment, optical marker 144 comprises a checkerboard pattern disposed external to the intraoral detector 120.

FIG. 15 illustrates example screen shots of five slices of a foot phantom using a free-form tomosynthesis imaging setup where x-ray source 110 was manually moved through 11 distinct positions relative to the foot phantom across an approximately 15 degree arc. FIGS. 16A-16B illustrate example screen shots of three slices of a hand phantom from two different depths using a free-form tomosynthesis imaging setup. The set of images in FIG. 16A (left) provide reconstructions from a stationary tomosynthesis device (e.g., chest tomosynthesis imaging device) and the set of images in FIG. 16B (right) provide reconstructions from a manual tomosynthesis device using a hand calibration phantom for source positioning in the middle and using optically determined geometry.

Accordingly, the optical geometry calibration devices, systems, and methods provided herein are advantageously unrestricted by a physically connected detector and source, which allows for portable 3D imaging using hand-held devices, the imaging of any size objects and immovable or dangerous objects. As provided in the figures herein, for example, error of utilizing an optical geometry calibration device, system, and/or method for tomosynthesis imaging is very small—sub millimeter accuracy is easily obtained, e.g., within a 3.5% deviation. Moreover, reconstruction using the optical method shows details that match up with standard reconstruction.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:

1. An imaging system with in situ real time determination of imaging geometries by which individual two-dimensional (2D) x-ray projection images are captured for three-dimensional (3D) image reconstruction, the imaging system comprising:
   an x-ray source;
   a detector positioned relative to the x-ray source, the detector being configured to obtain the individual 2D x-ray projection images of an object from the x-ray source;
   an optical-based in situ real time geometry calibration device to determine a spatial position and orientation of the x-ray source and the detector relative to the object in real time; and
   an image processing system configured to reconstruct a 3D structure of the object from the individual 2D x-ray projection images and associated imaging geometry parameters;
   wherein the x-ray source and the detector are mechanically decoupled from one another such that the imaging system is operable as a free-form setup.

2. The imaging system of claim 1, wherein the optical-based in situ real time geometry calibration device comprises multiple optical cameras and multiple markers, wherein the optical cameras and the markers are mounted on either the x-ray source or the detector, and each optical camera of the multiple optical cameras is configured to capture at least one photographic image of at least one corresponding marker of the multiple markers.

3. The imaging system of claim 2, wherein each of the multiple markers is an optical pattern including a black and white chessboard pattern.

4. The imaging system of claim 2, wherein each of the optical cameras is configured to capture at least one photographic image of a corresponding marker at each position where an individual 2D x-ray projection image of the object is taken, and wherein the image processing system is configured to compute the spatial position and orientation of the x-ray source and the detector relative to each other based on a comparison of the at least one photographic image of the corresponding marker to prior dimensions of the corresponding marker, prior relative positions of the optical cameras with respect to the x-ray source, and a relative position of the corresponding marker with respect to the detector.

5. The imaging system of claim 1, wherein the individual 2D x-ray projection images are taken over a limited angular range to reconstruct 3D tomosynthesis images of the object.

6. The imaging system of claim 1, wherein the detector is a flat panel detector or a multi-pixel detector.

7. The imaging system of claim 2, wherein the x-ray source is an x-ray source array containing multiple distributed focal spots.

8. The imaging system of claim 7, wherein each optical camera is configured to capture at least one photographic image of a corresponding marker at each relative position of the x-ray source with respect to the detector; and
   wherein the image processing system is configured to compute the spatial position and orientation of each x-ray focal spot and the x-ray source array relative to the detector based on a comparison of the at least one photographic image of the corresponding marker to prior dimensions of the corresponding marker, prior relative positions of a corresponding optical camera with respect to the x-ray source, a relative position of the corresponding marker with respect to the detector, and prior relative positions of focal spots in the x-ray source array.

9. The imaging system of claim 1, wherein the x-ray source and the detector are configured to be manually or mechanically moved to the plurality of spatial positions and orientations relative to one another to capture the individual 2D x-ray projection images.

10. The imaging system of claim 1, wherein the system is configured as a portable 3D imaging system for use in the field or in an emergency vehicle.

11. A free-form intra-oral x-ray imaging system for three-dimensional (3D) imaging of a facial cavity, the system comprising:
   an x-ray source freely positioned outside the facial cavity;
   an intra-oral x-ray detector mechanically detached from the x-ray source and positioned inside the facial cavity;
   a geometry calibration device comprising one or more optical cameras fixed to the x-ray source, each of the one or more optical cameras being configured to capture at least one photographic image of one or more optical markers fixed to the intra-oral x-ray detector when each x-ray image of the facial cavity is captured;
   an image processing system configured to determine a position of the x-ray source and the detector relative to each other and to the object being imaged for each projection image and to reconstruct a 3D structure of the object from the projection image and corresponding determined geometry parameters; and
   a control unit configured to coordinate an activation of one or more of the x-ray source or the one or more optical cameras.

12. The imaging system of claim 11, wherein the one or more optical markers is held at a position that is substantially fixed relative to the facial cavity while one or more of the x-ray source or the intra-oral x-ray detector is moved to multiple locations relative to the facial cavity.

13. The imaging system of claim 11, wherein the one or more optical markers comprises one or more geometrical patterns of the facial cavity such that the geometry calibration device is configured to detect the one or more geometrical patterns of the facial cavity.

14. The imaging system of claim 11, wherein the system is a computed tomography system with a reconfigurable and flexible imaging geometry, allowing collection of projection images with variable source-detector distances and flexible source trajectory.

15. A method of three-dimensional (3D) x-ray imaging of a facial cavity with real time geometry calibration using optical cameras and markers, the method comprising:
   positioning one or more optical marker relative to an intra-oral x-ray detector and inside the facial cavity, wherein the one or more optical marker is mechanically detached from the x-ray source,
   further positioning one or more optical camera relative to an x-ray source with predetermined position and orientation;
   moving the x-ray source and/or the x-ray detector into different positions relative the facial cavity;
   simultaneously capturing optical images of the one or more marker by the one or more optical camera and obtaining individual two-dimensional (2D) x-ray projection images of the facial cavity from a plurality of spatial positions and orientations of the x-ray source and/or the intra-oral x-ray detector relative to the facial cavity;
   using the optical image of the one or more marker to perform in situ real time geometry calibration to determine a spatial position and orientation of the x-ray source and the intra-oral x-ray detector relative to each other and the facial cavity, for each of the individual 2D x-ray projection images; and
   performing 3D image reconstruction of the object using the 2D x-ray projection images and associated geometry parameters.

16. The imaging system of claim 1, wherein the optical-based in situ real time geometry calibration device is configured to continuously monitor and calibrate a position of the detector and the x-ray source relative to the object been imaged.

17. The imaging system of claim 11, wherein multiple 2D x-ray projection images are obtained by the x-ray source, the x-ray source comprising an array of multiple distributed focal spots.

18. The imaging system of claim 17, wherein the multiple 2D x-ray projection images are obtained by positioning the x-ray source relative to the intra-oral x-ray detector at different positions.

* * * * *